(12) United States Patent
Chen et al.

(10) Patent No.: US 10,245,313 B2
(45) Date of Patent: Apr. 2, 2019

(54) DNA MOTIF COMPOUNDS AND METHODS FOR INDUCING SPECIFIC ANTIBODIES AND CELLULAR IMMUNITY

(71) Applicants: VERSITECH LIMITED, Hong Kong (CN); Center for Public Health Research, Nanjing University, Nanjing (CN)

(72) Inventors: Zhiwei Chen, Hong Kong (CN); Xilin Wu, Hong Kong (CN); Zhiwei Wu, Nanjing (CN)

(73) Assignees: VERSITECH LIMITED, Hong Kong (CN); NANJING UNIVERSITY, Nanjing (CN)

(*) Notice: Subject to any disclaimer, the term of this patent is extended or adjusted under 35 U.S.C. 154(b) by 127 days.

(21) Appl. No.: 14/921,323

(22) Filed: Oct. 23, 2015

(65) Prior Publication Data

US 2016/0114028 A1 Apr. 28, 2016

Related U.S. Application Data

(60) Provisional application No. 62/068,316, filed on Oct. 24, 2014.

(51) Int. Cl.
*A61K 39/21* (2006.01)
*A61K 39/12* (2006.01)
*A61K 39/00* (2006.01)

(52) U.S. Cl.
CPC .............. *A61K 39/21* (2013.01); *A61K 39/12* (2013.01); *A61K 2039/53* (2013.01); *A61K 2039/575* (2013.01); *C12N 2740/16034* (2013.01); *C12N 2740/16234* (2013.01)

(58) Field of Classification Search
None
See application file for complete search history.

(56) References Cited

U.S. PATENT DOCUMENTS

| 2003/0157135 A1* | 8/2003 | Tsuji | A61K 39/015 424/278.1 |
| 2012/0121634 A1* | 5/2012 | Chen | A61K 39/21 424/188.1 |

FOREIGN PATENT DOCUMENTS

WO WO/2013/040564 3/2013

OTHER PUBLICATIONS

Burton and Moore, Nature Medicine, 1998, 4(5):495-498.*
Desrosiers, Nature Medicine, 2004, 10(3):221-223.*
Matthews et al., 1987, AIDS Research and Human Retroviruses, 3(1):197-206.*
GenBank Accession No. ADI59551.1 (Jun. 16, 2010).*
Brown, A. J. L., S. D. W. Frost, W. C. Mathews, K. Dawson, N. S. Hellmann, E. S. Daar, D. D. Richman and S. J. Little (2003). "Transmission fitness of drug-resistant human immunodeficiency virus and the prevalence of resistance in the antiretroviral-treated population." Journal of Infectious Diseases 187(4): 683-686.
Lustig JV, Rieger HL, Kraft SC et al. "Humoral and cellular responses to native antigen following oral and parenteral immunization with lipid-conjugated bovine serum albumin." Cell Immunol. Jun. 1, 1976; 24(1): 164-72.
Mascola, J. R. and D. C. Montefiori (2010). "The Role of Antibodies in HIV Vaccines." Annual Review of Immunology, vol. 28. Palo Alto, Annual Reviews. 28: 413-444.
Mowat AM, Donachie AM, Reid G, Jarrett O. "Immune-stimulating complexes containing Quil A and protein antigen prime class I MHC-restricted T lymphocytes in vivo and are immunogenic by the oral route." Immunology. Mar. 19991; 72(3): 317-22.
Pearson WR, Lipman DJ. "Improved tools for biological sequence comparison." Proc Natl Acad Sci. 1988; 85: 2444-2448.
Qi, Y., B. Q. Zhang, Z. Shen and Y. H. Chen (2009). "Candidate Vaccine Focused on a Classical Swine Fever Virus Epitope Induced Antibodies with Neutralizing Activity." Viral Immunology 22(3): 205-213.
Shang, H., X. Han, X. Shi, T. Zuo, M. Goldin, D. Chen, B. Han, W. Sun, H. Wu, X. Wang and L. Zhang (2011). "Genetic and Neutralization Sensitivity of Diverse HIV-1 env Clones from Chronically Infected Patients in China." Journal of Biological Chemistry 286(16): 14531-14541.
Thompson JD, Higgins DG, Gibson TJ. "CLUSTAL W: improving the sensitivity of progressive multiple sequence alignment through sequence weighting, position-specific gap penalties and weight matrix choice." Nucleic Acids Res. Nov. 11, 1994; 22(22): 4673-80.
Ulmer JB, Donnelly JJ, Parker SE, et al. (1993). "Heterologous protection against influenza by injection of DNA encoding viral protein." Science 259(5102):1745-1749.
Zhou, J., A. K. Cheung, Z. Tan, H. Wang, W. Yu, Y. Du, Y. Kang, X. Lu, L. Liu, K. Y. Yuen and Z. Chen (2013). "PD1-based DNA vaccine amplifies HIV-1 GAG-specific CD8+ T cells in mice." Journal of Clinical Investigation.
McLellan, J.S. et al., Structure of HIV-1 gp 120 V1/V2 domain with broadly neutralizing antibody PG9, Nature, 2011, 480 (7377): p. 336-U86.

* cited by examiner

*Primary Examiner* — Nicole Kinsey White
(74) *Attorney, Agent, or Firm* — Leason Ellis LLP

(57) ABSTRACT

The present invention relates to the field of applied immunotechnology and medicine. More specifically, it relates to DNA motif vaccine design, glyco-DNA motif vaccine design, and immunogen design for producing antibodies against an epitope of arbitrary sequences or polysaccharide epitope, particularly those epitopes against which it is otherwise very difficult to induce antibodies, such as those of HIV-1. The present invention also relates to immunogen design to induce robust cellular and humoral immunity.

9 Claims, 22 Drawing Sheets

Specification includes a Sequence Listing.

FIG. 1C

| | |
|---|---|
| CTM12 | KGLVQAGPGFYF-GLI |
| CTM13 | ICAWTGGPGFPL-FIV |
| CTM14 | NHDHMNGPGM-SF-IN |
| CTM15 | TAPRMKGPGTFP-RSY |
| CTM16 | NLLARYGPGFVL-TCF |
| OVAM01 | ------AGPGPFC-GYV |
| OVAM05 | ------GPGRFW-LSL |
| OVAM06 | SSPYTLGPGLY----LG |
| OVAM07 | ------IGPGVWD-VVI |
| OVAM09 | TST-RYGPGSLF-WGR |
| OVAM10 | ------PGPGFVF-LYF |
| OVAM11 | VLHSYKGPGCLA-SSL |
| OVAM15 | FD-NIQGPGVAIAYFI |
| OVAM16 | FPLRSRGPGFPS-FLS |
| OVAM18 | VSPPLEGPGGLA-CWL |
| OVAM21 | ------GPGIILS-LCP |
| OVAM23 | IGLASYGPGYHH-LIR |
| OVAM24 | ------HAGPGVLL-FSW |
| OVAM25 | FII-GFGPGSDD-VFS |
| OVAM26 | FPSARAGPGPFC-GYV |
| OVAM27 | ------HAGPGVLL-FSW |
| OVAM28 | TQTRDKGPGSFF-SAG |
| OVAM29 | TQSRDKGPGSFF-SVG |
| OVAM30 | VGMNCNGPGTLF-GCN |
| PDM06 | ------GPGLST-LVI |
| PDM08 | WSDTLAGPGVWT-YFI |

FIGS. 6A-B
A
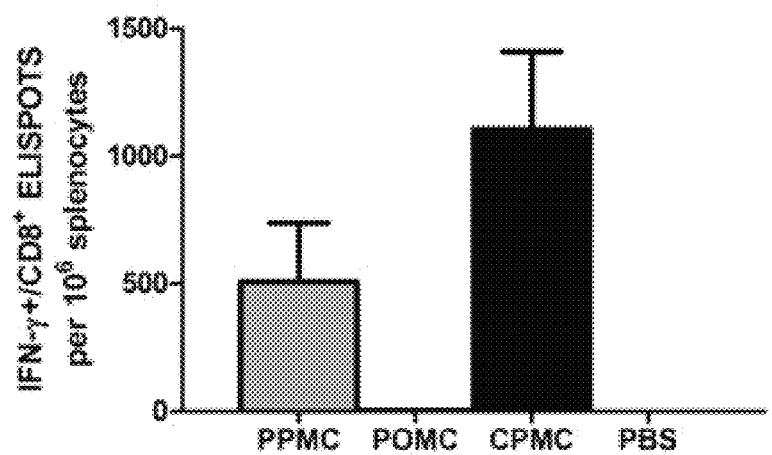
B
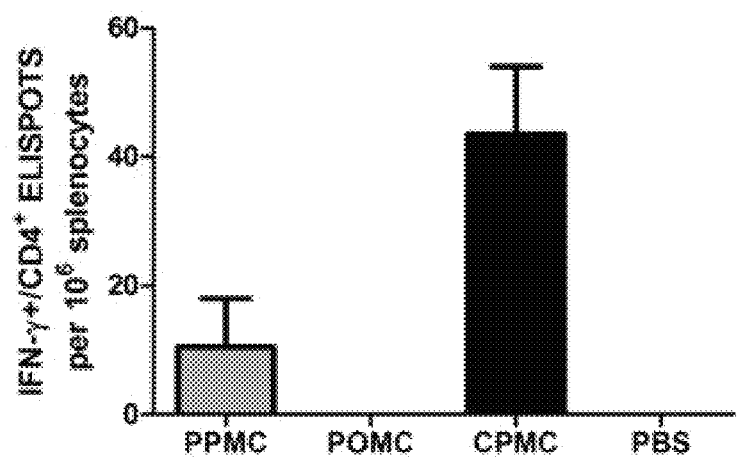

FIG. 7D

| Project | Project ID | Motif sequence of amino acid residues | SEQ ID |
|---|---|---|---|
| N168 | 168M01 | xxxxx NCSF NITT xxxx | SEQ ID NO 1 |
|  | 168M02 | xxxxx NxSx NxTT xxxx | SEQ ID NO 2 |
|  | 168M03 | xxxxx xxSx NxTT xxxx | SEQ ID NO 3 |
| N295 | 295M01 | xxxxx INCTRP xxxxx | SEQ ID NO 4 |
| N332 | 332M01 | xxxxx AHCNxS xxxxx | SEQ ID NO 5 |
|  | 332M02 | xxxxx AxCNxS xxxxx | SEQ ID NO 6 |

Figure 11:
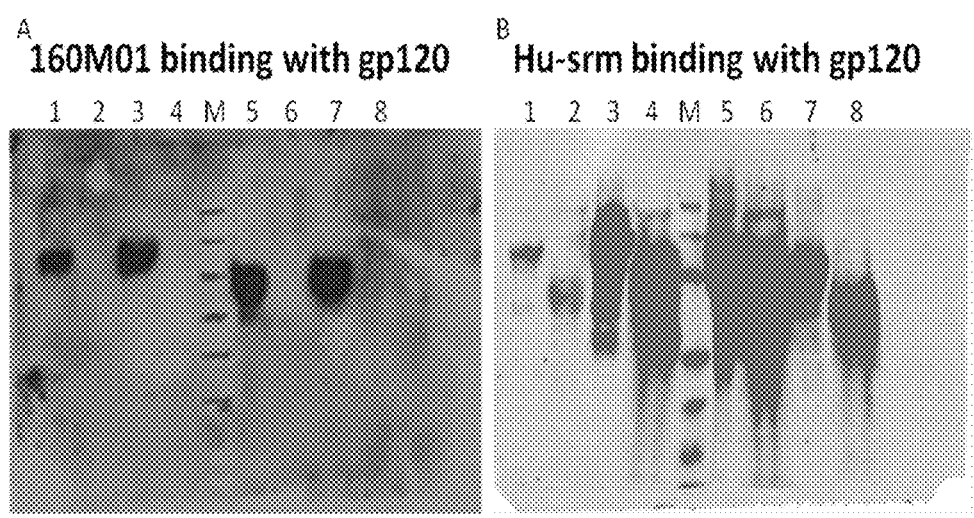

FIGS. 11A-B

```
                         SEQUENCE LISTING

<160> NUMBER OF SEQ ID NOS: 48

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (14)..(17)
<223> OTHER INFORMATION: Any amino acid

<400> SEQUENCE: 1

Xaa Xaa Xaa Xaa Xaa Asn Cys Ser Phe Asn Ile Thr Thr Xaa Xaa Xaa
1               5                   10                  15

Xaa

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(17)
<223> OTHER INFORMATION: Any amino acid

<400> SEQUENCE: 2

Xaa Xaa Xaa Xaa Xaa Asn Xaa Ser Xaa Asn Xaa Thr Thr Xaa Xaa Xaa
1               5                   10                  15

Xaa

<210> SEQ ID NO 3
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(17)
<223> OTHER INFORMATION: Any amino acid

<400> SEQUENCE: 3

Xaa Xaa Xaa Xaa Xaa Xaa Xaa Ser Xaa Asn Xaa Thr Thr Xaa Xaa Xaa
1               5                   10                  15

Xaa

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (12)..(16)
<223> OTHER INFORMATION: Any amino acid

<400> SEQUENCE: 4

Xaa Xaa Xaa Xaa Xaa Ile Asn Cys Thr Arg Pro Xaa Xaa Xaa Xaa Xaa
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (12)..(16)
<223> OTHER INFORMATION: Any amino acid

<400> SEQUENCE: 5

Xaa Xaa Xaa Xaa Xaa Ala His Cys Asn Ile Ser Xaa Xaa Xaa Xaa Xaa
1               5                   10                  15

<210> SEQ ID NO 6
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(16)
<223> OTHER INFORMATION: Any amino acid

<400> SEQUENCE: 6

Xaa Xaa Xaa Xaa Xaa Ala Xaa Cys Asn Xaa Ser Xaa Xaa Xaa Xaa Xaa
1               5                   10                  15

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other

<400> SEQUENCE: 7
ggccccggcn nbnnbnnbnn bnnbnnbatc ctgatgcagt acatcaagg              49

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
```

```
<222> LOCATION: (8)..(9)
<223> OTHER INFORMATION: a, c, t, g, unknown or other
<220> FEATURE:
<221> NAME/KEY: modified_base
<222> LOCATION: (11)..(12)
<223> OTHER INFORMATION: a, c, t, g, unknown or other
<220> FEATURE:
<221> NAME/KEY: modified_base
<222> LOCATION: (14)..(15)
<223> OTHER INFORMATION: a, c, t, g, unknown or other
<220> FEATURE:
<221> NAME/KEY: modified_base
<222> LOCATION: (17)..(18)
<223> OTHER INFORMATION: a, c, t, g, unknown or other

<400> SEQUENCE: 8
vnnvnnvnnv nnvnnvnnct cgagcggcaa aactcttg                              38

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other
<220> FEATURE:
<221> NAME/KEY: modified_base
<222> LOCATION: (11)..(12)
<223> OTHER INFORMATION: a, c, t, g, unknown or other
<220> FEATURE:
<221> NAME/KEY: modified_base
<222> LOCATION: (14)..(15)
<223> OTHER INFORMATION: a, c, t, g, unknown or other
<220> FEATURE:
<221> NAME/KEY: modified_base
<222> LOCATION: (17)..(18)
<223> OTHER INFORMATION: a, c, t, g, unknown or other

<400> SEQUENCE: 9
vnnvnnvnnv nnvnnvnnct cgagcggagg ggaaaca                               37

<210> SEQ ID NO 10
<211> LENGTH: 9
<212> TYPE: PRT
<213> ORGANISM: Human immunodeficiency virus 1

<400> SEQUENCE: 10

Ala Met Gln Met Leu Lys Asp Thr Ile
1               5

<210> SEQ ID NO 11
<211> LENGTH: 20
<212> TYPE: PRT
<213> ORGANISM: Human immunodeficiency virus 1

<400> SEQUENCE: 11

Thr Ser Asn Pro Pro Ile Pro Val Gly Asp Ile Tyr Lys Arg Trp Ile
1               5                   10                  15

Ile Leu Gly Leu
```

```
<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Met Gln Met Leu Lys Asp Thr Ile
1               5

<210> SEQ ID NO 13
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other

<400> SEQUENCE: 13
aactgctcct tcaacatcac caccnnbnnb nnbnnbnnbn nbatcctgat gcagtacatc    60
aagg                                                                64

<210> SEQ ID NO 14
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
```

<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other

<400> SEQUENCE: 14
aacnnbtccn nbaacnnbac caccnnbnnb nnbnnbnnbn nbatcctgat gcagtacatc    60
aagg                                                                64

<210> SEQ ID NO 15
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other

<400> SEQUENCE: 15
nnbnnbtccn nbaacnnbac caccnnbnnb nnbnnbnnbn nbatcctgat gcagtacatc    60
aagg                                                                      64

<210> SEQ ID NO 16
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 16
atcaactgca cccgccccnn bnnbnnbnnb nnbnnbatcc tgatgcagta catcaagg      58

<210> SEQ ID NO 17
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 17
gcccactgca acatctccnn bnnbnnbnnb nnbnnbatcc tgatgcagta catcaagg      58

<210> SEQ ID NO 18

```
<211> LENGTH: 58
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 18
gccnnbtgca acnnbtccnn bnnbnnbnnb nnbnnbatcc tgatgcagta catcaagg     58

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other
<220> FEATURE:
<221> NAME/KEY: modified_base
<222> LOCATION: (11)..(12)
<223> OTHER INFORMATION: a, c, t, g, unknown or other
<220> FEATURE:
<221> NAME/KEY: modified_base
<222> LOCATION: (14)..(15)
<223> OTHER INFORMATION: a, c, t, g, unknown or other
<220> FEATURE:
<221> NAME/KEY: modified_base
<222> LOCATION: (17)..(18)
<223> OTHER INFORMATION: a, c, t, g, unknown or other

<400> SEQUENCE: 19
vnnvnnvnnv nnvnnvnnct cgagcggagg ggaaaca                            37
```

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Gly Leu Val Gln Ala Gly Pro Gly Phe Tyr Phe Gly Leu Leu
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Cys Ala Trp Thr Gly Gly Pro Gly Phe Pro Leu Phe Ile Val
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn His Asp His Met Asn Gly Pro Gly Met Ser Phe Ile Trp
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Ala Pro Arg Met Lys Gly Pro Gly Thr Phe Pro Arg Ser Tyr
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Leu Leu Ala Arg Tyr Gly Pro Gly Phe Val Leu Thr Cys Phe
1               5                   10                  15

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 25

Ala Gly Pro Gly Pro Phe Cys Gly Tyr Val
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Pro Gly Arg Phe Trp Leu Ser Leu
1               5

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ser Pro Tyr Thr Leu Gly Pro Gly Leu Tyr Leu Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Gly Pro Gly Val Trp Asp Val Val Ile
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Ser Thr Arg Tyr Gly Pro Gly Ser Leu Phe Trp Gly Arg
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Gly Pro Gly Phe Val Phe Leu Tyr Phe
1               5                   10

<210> SEQ ID NO 31
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Leu His Ser Tyr Lys Gly Pro Gly Cys Leu Ala Ser Ser Leu
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Asp Asn Ile Gln Gly Pro Gly Val Ala Thr Ala Tyr Phe Ile
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Pro Leu Arg Ser Arg Gly Pro Gly Phe Pro Ser Phe Leu Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Ser Pro Pro Leu Glu Gly Pro Gly Gly Leu Ala Cys Trp Leu
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Pro Gly Ile Leu Ser Leu Cys Pro
1               5

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Gly Leu Ala Ser Tyr Gly Pro Gly Tyr His His Leu Ile Arg
```

-continued

```
<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Ala Gly Pro Gly Val Leu Leu Phe Ser Trp
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Ile Ile Gly Phe Gly Pro Gly Ser Asp Asp Val Phe Ser
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Pro Ser Ala Arg Ala Gly Pro Gly Pro Phe Cys Gly Tyr Val
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Gln Thr Arg Asp Lys Gly Pro Gly Ser Phe Phe Ser Ala Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Gln Ser Arg Asp Lys Gly Pro Gly Ser Phe Phe Ser Val Gly
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 42

Val Gly Met Asn Cys Asn Gly Pro Gly Thr Leu Phe Gly Cys Asn
1               5                   10                  15

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Pro Gly Leu Ser Thr Leu Val Ile
1               5

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Ser Asp Thr Leu Ala Gly Pro Gly Val Trp Thr Tyr Phe Ile
1               5                   10                  15

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Pro Gly Arg
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Leu Gly Arg
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gln Gly Arg
1

<210> SEQ ID NO 48
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Pro Gly Gln
1
```

DNA MOTIF COMPOUNDS AND METHODS FOR INDUCING SPECIFIC ANTIBODIES AND CELLULAR IMMUNITY

CROSS-REFERENCE TO RELATED APPLICATIONS

This application claims priority to U.S. provisional application Ser. No. 62/068,316, filed Oct. 24, 2014, which is hereby incorporated by reference in its entirety.

1. FIELD

The present application relates to the field of applied immunotechnology and medicine. More specifically, it relates to DNA motif vaccine design or immunogen design for producing antibodies against an epitope of arbitrary sequences or a polysaccharide epitope for which it is difficult to induce antibodies.

2. BACKGROUND

Human immunodeficiency virus type 1 (HIV-1) is a highly mutated virus, which can mutate in different viral particle/envelope regions, at different infection stages, and even exhibit different mutations within the same patient. This high mutation rate is the major reason for the many failures to generate a vaccine against HIV-1. Antibodies induced by numerous experimental vaccines have failed to bind and neutralize HIV-1 viral particles as the HIV-1 virus mutates to escape capture by targeting antibodies. Broadly neutralizing antibodies (bNAbs), such as b12, 447-52D, PGT128, VRC01, 10E8, have been shown to protect in passive immunization and challenge studies in non-human primates. However, to date, there are no vaccines capable of inducing broadly neutralizing antibodies against highly conserved HIV-1 viral epitopes due to the weak immunogenicity of these regions.

In addition, the surface antigen of HIV-1, gp120, is covered by an extensive array of N-linked glycans. These host-derived carbohydrate structures comprise half of the mass of gp120 and shield much of the underlying protein surface, which play essential functional roles in infection and immune evasion. Broadly neutralizing antibodies such as PG9, PG16, PGT128 and 2G12 that bind to the host-derived carbohydrate of gp120 have been shown to provide protection against HIV infection. These results suggest that a vaccine that induces broadly neutralization antibodies to bind against the epitope of carbohydrate of gp120 could prevent HIV infection. However, there are no effective methods to synthesize these host-derived polysaccharides in vitro presenting a similar configuration as host-derived carbohydrate structures of gp120 in vivo. Additionally, the host-derived polysaccharide belongs to T cell independent antigens, which exhibit weak immunogenicity. Thus, it is difficult to induce antibodies specific for host-derived carbohydrates. Despite the various types of vaccines generated to date—including attenuating virus, virus like particle, protein and peptide—all of them have failed to protect against highly mutated and heavily glycosylated HIV-1 infection.

Peptide motif immunization is a technique that is capable of inducing broadly neutralizing antibodies (bNAbs) against highly conserved and functional domains of HIV-1 envelope proteins in the animal models of HIV including in mice, rabbits and rhesus monkeys. Although bNAbs against the weak immunogenicity epitopes were induced by peptide motif immunization in these examples and models as described in WO/2013/040564, it failed to elicit antibodies against the host-derived carbohydrate which was difficult to synthesize in vitro to ensure that its configuration was similar with the native status modified in vivo. In addition, the half-life of the peptide antigen was far shorter than DNA antigen and it failed to induce cellular immunity against HIV-1 infection. Despite that robust cellular immunity against HIV has been induced by a previously constructed plasmid of PD1-P24, neutralization antibodies against HIV-1 have not been elicited via such method. To date, there are no successful vaccines against HIV-1 exhibiting robust cellular immunity. A large number of data indicates that bNAbs are important for inhibiting of HIV-1 infection. Thus, there is a continuing need for an HIV-1 vaccine that induces bNAbs and also exhibits robust cellular immunity against HIV-1.

3. SUMMARY

An object of the disclosure is to provide DNA motif vaccines for eliciting an immune response against HIV. More specifically, the present application provides for DNA motif vaccines and glyco-DNA motif vaccines for inducing broadly neutralizing antibodies (bNAbs) against HIV.

According to an aspect of the invention, the DNA motif vaccine comprises at least one plasmid including a nucleic acid sequence, the nucleic acid sequence encoding a first plurality of amino acid residues in the center of the motif sequence, and a second and third plurality of random amino acid residues in the regions flanking the first plurality, such that the first plurality of amino acid residues includes an amino acid sequence GPG.

According to another aspect of the invention, the DNA motif vaccine can comprise a plasmid having a pVAX vector backbone. In at least one aspect, the plasmid can be selected from a group consisting of PD1-P24-pVAX, PD1-OVA-pVAX, and CTLA4-P24-pVAX.

According to another aspect, the plasmid of the DNA motif vaccine can includes a primer selected from the group consisting of:

```
Fc Forward
                                            (SEQ ID NO: 7)
5' (GGC CCCGGC NNB NNB NNB NNB NNB NNB

ATCCTGATGCAGTACATCAAGG) 3';

P24 backward
                                            (SEQ ID NO: 8)
5' (VNN VNN VNN VNN VNN VNN CTCGAGCGGCAAAACTCTTG)

3';
and

OVA backward
                                            (SEQ ID NO: 9)
5' (VNN VNN VNN VNN VNN VNN

CTCGAGCGGAGGGGAAACA) 3'.
```

According to another aspect, the length of the amino acid residues of the first plurality can range from 3 to 30 amino acid residues in the center of the motif sequence.

According to another aspect, the random amino acid residues can range from 5-50 amino acid residues and be encoded by a nucleotide fragment ranging in length of from 15-150 nucleotides.

According to another aspect, a glyco-DNA motif vaccine can be provide, where the glyco-DNA motif vaccine comprises a plasmid selected from the group consisting of 160M01, 160M02, 160M03, 295M01, 332M01, and 332M02, and the plasmid comprises a glycosylation motif gene encoding motif peptide NxS/T, wherein the glyco-DNA motif vaccine induces antibodies specific for gp120.

According to a further aspect, the glycosylation motif peptide NxS/T can be modified to add host-derived carbohydrates on an amino acid residue of Asparagine (N) for facilitating in vivo peptide expression.

According to another aspect, the glyco-DNA motif vaccine can induce antibodies against a glycogen epitope to inhibit viral or bacterial infections, including HIV infections.

According to another aspect, the plasmid of the glyco-DNA motif vaccine can include a primer selected from the group consisting of:

```
                                          (SEQ ID NO: 13)
AACTGCTCCTTCAACATCACCACCNNBNNBNNBNNBNNBNNBATCCTGAT

GCAGTACATCAAGG;

(SEQ ID NO: 14)
AACNNBTCCNNBAACNNBACCACCNNBNNBNNBNNBNNBNNBATCCTGAT

GCAGTACATCAAGG;

(SEQ ID NO: 15)
NNBNNBTCCNNBAACNNBACCACCNNBNNBNNBNNBNNBNNBATCCTGAT

GCAGTACATCAAGG;

(SEQ ID NO: 16)
ATCAACTGCACCCGCCCCNNBNNBNNBNNBNNBNNBATCCTGATGCAGTA

CATCAAGG;

(SEQ ID NO: 17)
GCCCACTGCAACATCTCCNNBNNBNNBNNBNNBNNBATCCTGATGCAGTA

CATCAAGG;

(SEQ ID NO: 18)
GCCNNBTGCAACNNBTCCNNBNNBNNBNNBNNBNNBATCCTGATGCAGTA

CATCAAGG;
and (SEQ ID NO: 19)
VNN VNN VNN VNN VNN VNN CTCGAGCGGAGGGGAAACA.
```

According to another aspect, the glyco-DNA motif vaccine comprises the plasmid 160M01. According to a further aspect, the plasmid 160M01 can be constructed by inserting the motif gene coding the glycosylation peptide of N160 in HIV gp120.

According to another aspect, the plasmid of the glyco-DNA motif vaccine is a PD1-p24 plasmid with a pVAX backbone.

According to another aspect, the present invention provides method of inhibiting HIV-1 infection comprising administering a DNA motif vaccine to a patient in need thereof. According to a further aspect, the method comprises administering a DNA motif vaccine having a plasmid 160M01.

According to another aspect, the present invention provides a method of inducing a cellular and humoral immune response in a patient, comprising administering a DNA motif vaccine.

According to another aspect, the present invention provides a method of DNA motif immunization, comprising immunizing an animal model or human subject with a DNA motif vaccine.

According to another aspect, the present invention provides a kit for inducing broadly neutralizing antibodies against HIV, where the kit comprises a therapeutically effective amount of a DNA motif vaccine. According to a further aspect, the DNA motif vaccine of the kit can include a primer selected from the group consisting of SEQ ID NO: 7, 8, and 9.

According to another aspect, the present invention provides a kit for inducing broadly neutralizing antibodies against HIV, the kit comprising a therapeutically effective amount of a glyco-DNA motif vaccine. According to a further aspect, the glyco-DNA motif vaccine of the kit can include a primer selected from the group consisting of SEQ ID NO: 13, 14, 15, 16, 17, 18, and 19.

4. BRIEF DESCRIPTION OF THE DRAWING FIGURES

Figure 1A:
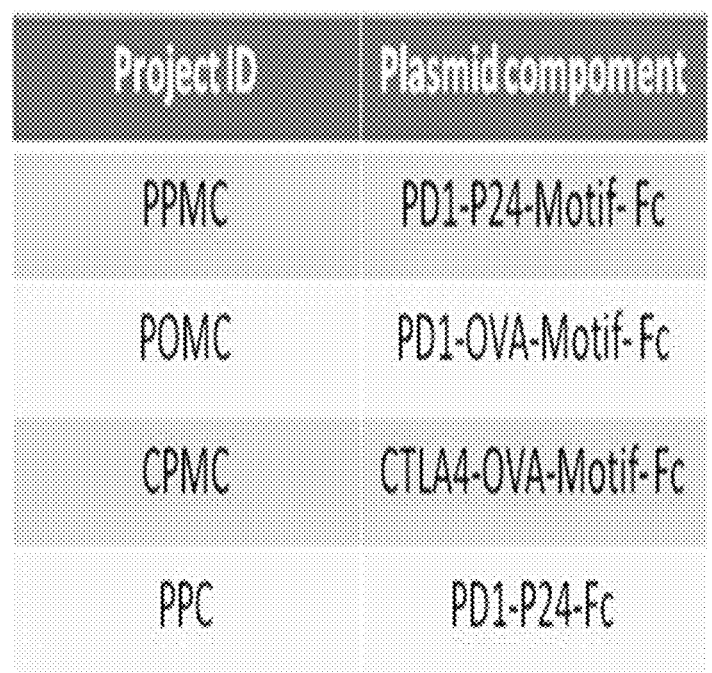
Figure 1B:
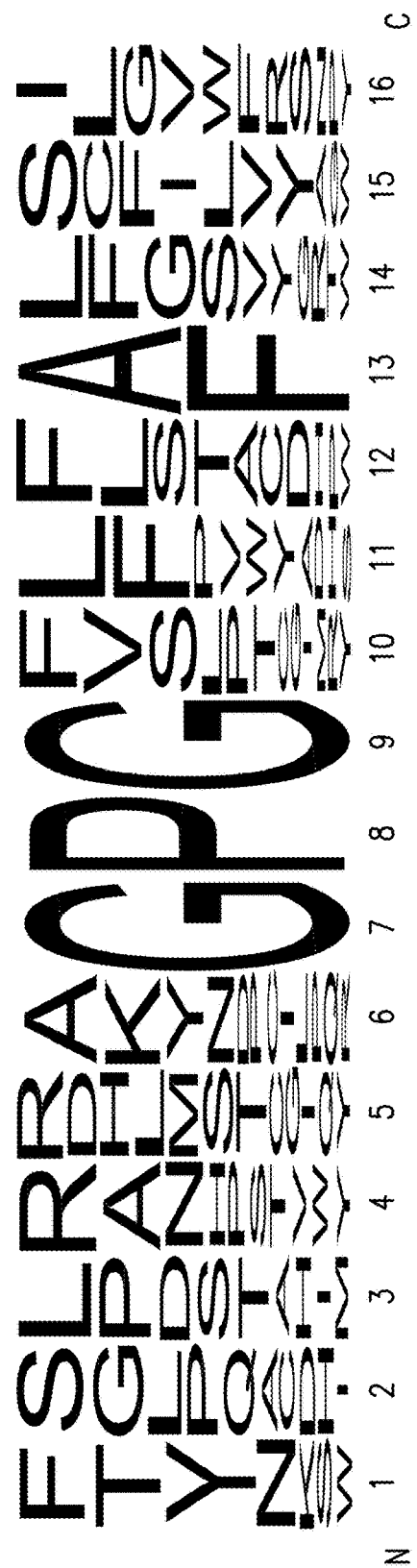

FIGS. 1A-C include a table (FIG. 1A) of the four DNA motif plasmids along with the sequence confirmation (FIG. 1B) of the motif sequence (GPG). The four plasmid constructs shown in FIG. 1A were verified by sequencing. FIG. 1A shows the components of each of the four DNA motif plasmids including the three new DNA motif plasmid libraries, which were established in the background of pVAX plasmid, and which all contained the inserted gene motif "GPG". Plasmid PPC was used as a control since it lacked the inserted motif gene. In FIG. 1B, the amino acid sequence encoded by the inserted gene motif in the PPMC plasmid was determined by sequencing and was aligned by software of Clustalw. It is shown in the format of weblogo. The height of amino acid residues indicates the conserved rate in different plasmid clones (with higher letters indicated greater conservation). The X axis indicates the location of amino acid residues encoded by the inserted gene. FIG. 1C is a table of amino acid sequencing results from representative plasmid of motif library containing the motif sequence GPG (SEQ ID NOS 20-39, 37 and 40-44, respectively, in order of appearance).

Figure 2:
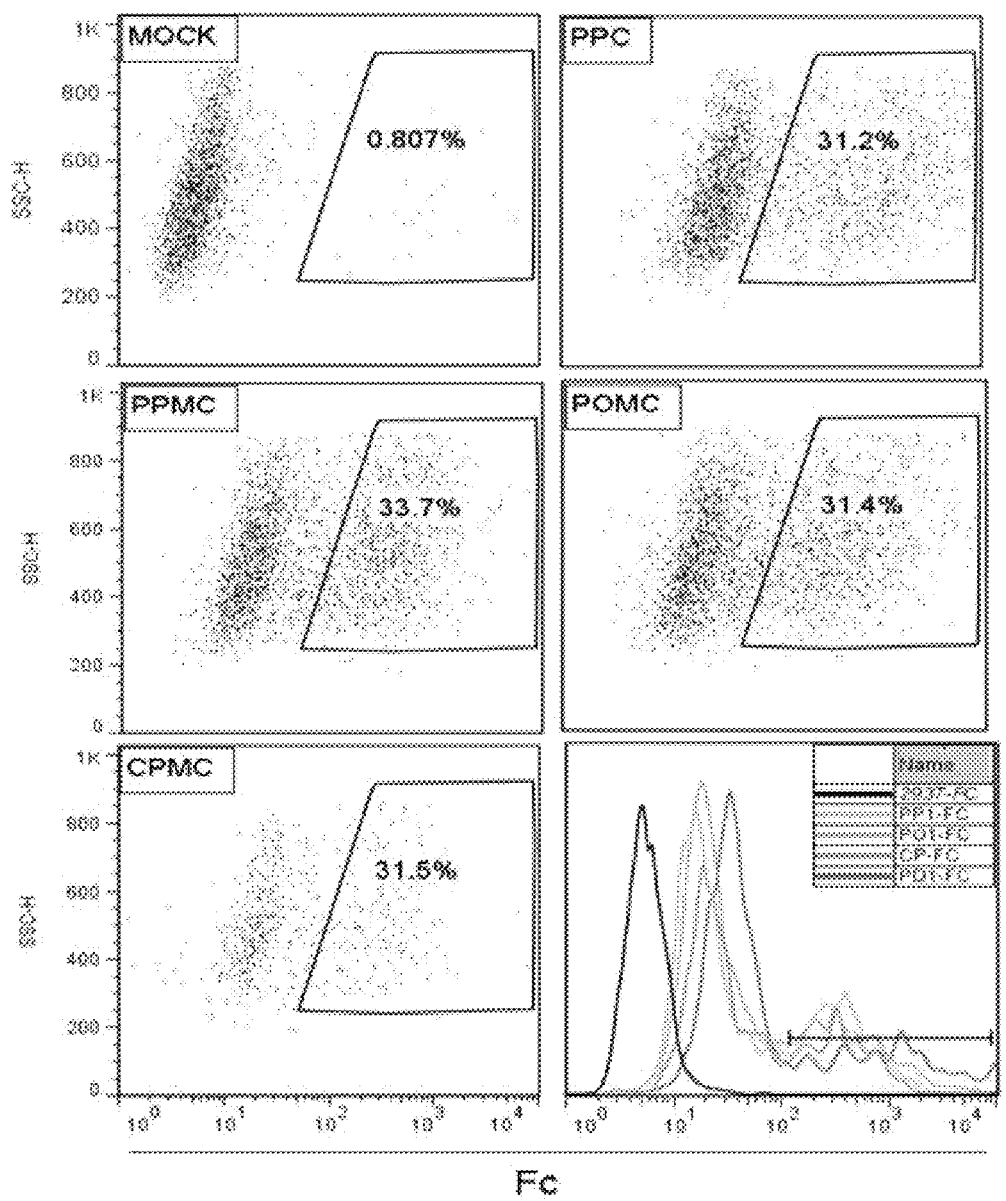

FIG. 2 shows fluorescence-activated cell sorting (FACS) protein expression results for the 4 plasmids. For the FACS analysis, 293T cells were transiently transfected with each different plasmid. The MOCK transfection was taken as negative control without plasmid and PPC was the background plasmid used as positive control for protein expression, as previously characterized. The PPMC, POMC and CPMC plasmids are presently constructed DNA motif vaccine plasmids, each containing an inserted gene motif encoded the GPG amino acid motif. FACS measures the expression of protein. The first five graphs are the dot spot diagrams examined by flow cytometry, and the last graph depicts the histogram of each corresponding plasmid with the solid black line as the negative control.

Figure 3:
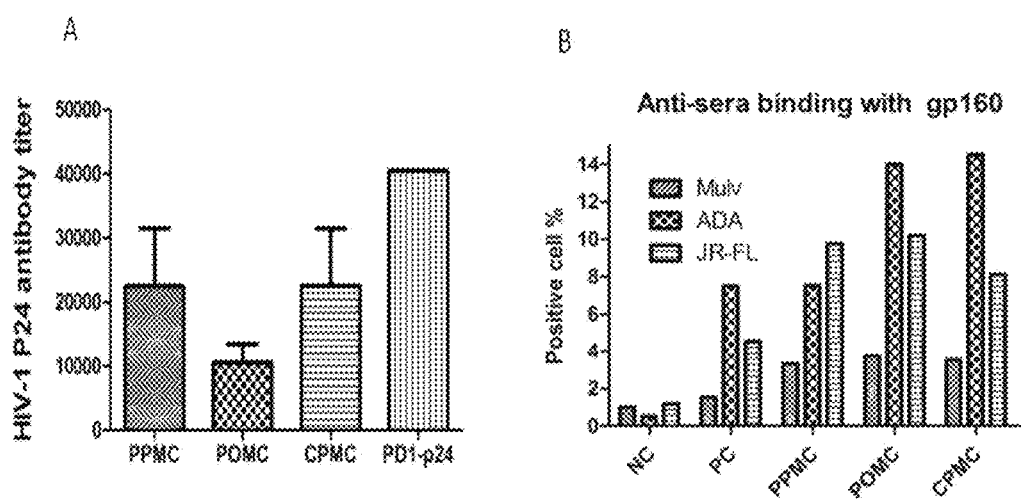

FIGS. 3A-B are graphs illustrating the generation of anti-sera from using the three DNA motif vaccine plasmids and control plasmid as immunogens. FIG. 3A shows the titer of anti-sera against the HIV-1 P24 detected by ELISA. FIG. 3B show anti-sera binding with gp160 from different subtypes of HIV on the 293T cell examined by flow cytometry, on samples generated using the three DNA motif vaccine plasmids and control plasmid used as immunogens.

Figure 4:
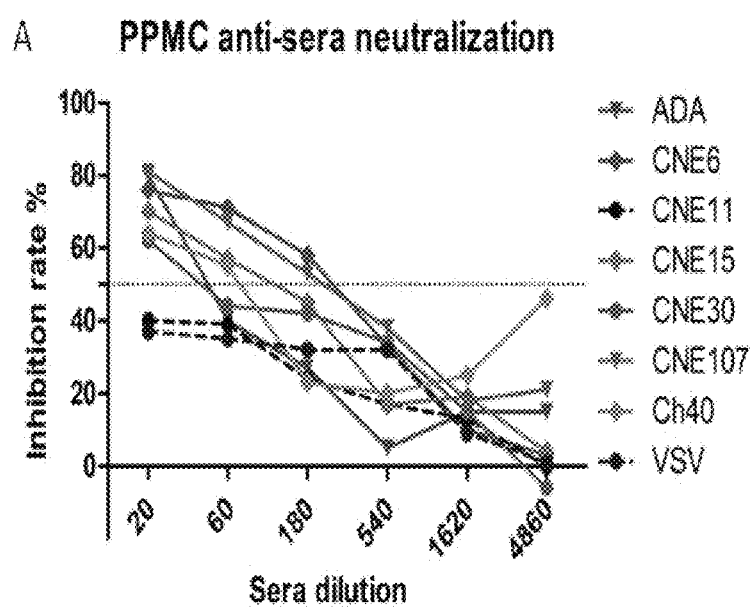

FIGS. 4A-B show the results of a neutralizing assay, specifically a graph and a table illustrating the characterization of anti-sera that neutralizes different subtypes of HIV. In FIG. 4A, PPMC plasmid resulted in the production of anti-sera that neutralized different subtypes of HIV (the dotted line is the control). FIG. 4B is a summary table listing the ND50 of different anti-sera against HIV pseudovirus. The darker shaded columns under ND50 represent the ND50 that was more than 40 dilution, and 4E10 is a well-known bNAb used as a positive control. FIG. 4B discloses SEQ ID NOS 45-48, 48, 45 and 45, respectively, in order of appearance.

Figure 5:
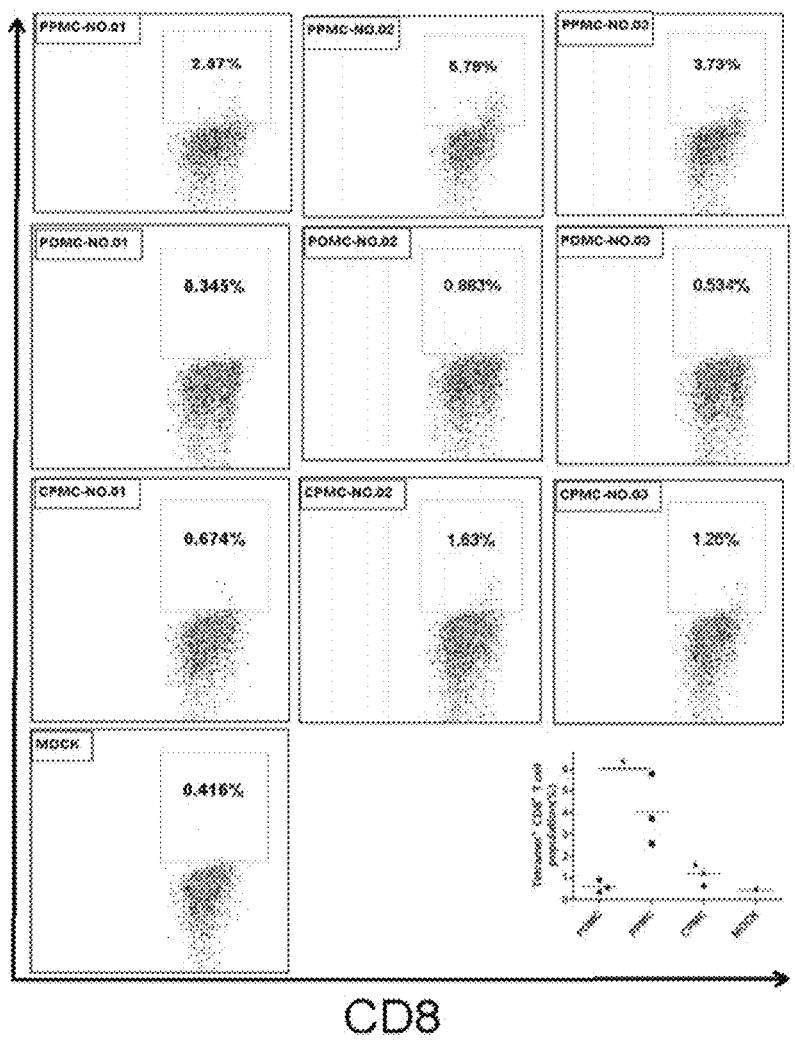

FIG. 5 shows flow cytometric data of DNA motif vaccine induced p24-specific tetramer-positive and long-term memory CD8+ T cell responses. Specifically, the flow cytometric plots show HIV-1 p24-specificH2-Kd-AMQM-LKDTI-PE tetramer ("AMQMLKDTI" disclosed as SEQ ID NO: 12) staining of CD8+ T cell populations 2 weeks after the final immunization, and the data is represented as a column graph in the last panel.

FIGS. 6A-B are graphs showing the comparison of DNA motif elicited antigen specific immunity in mice models. BALB/c mice were vaccinated with 100 μg DNA i.m/EP according to the immunization schedule. In FIGS. 6A-B, IFN-γ-producing CD8+ cells (FIG. 6A) and CD4+ cells (FIG. 6B) were measured by ELISPOT assay inBALB/c splenocytes stimulated using the specific peptides GAG A-I and GAG 26, respectively.

Figure 7A:
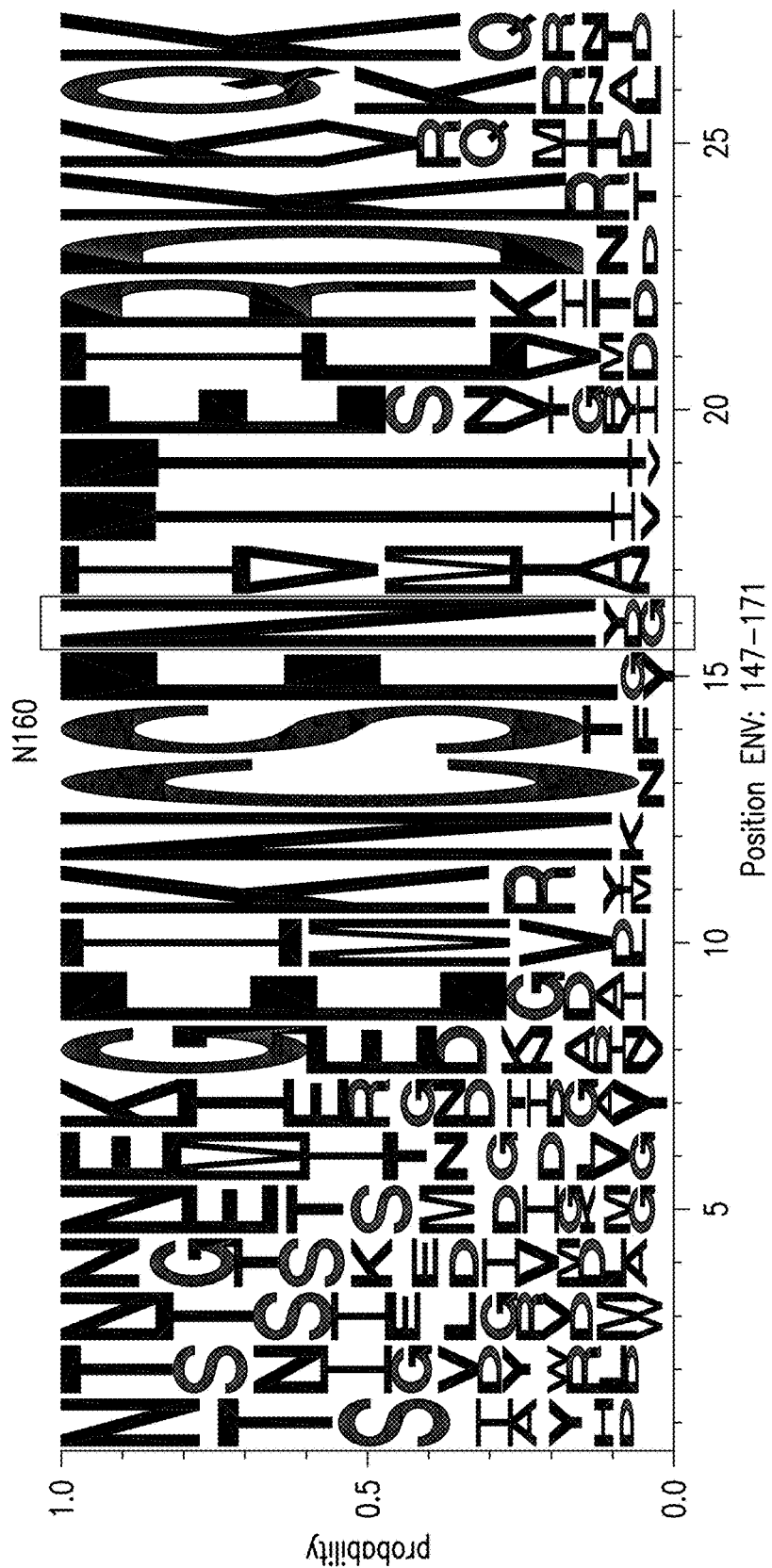
Figure 7B:
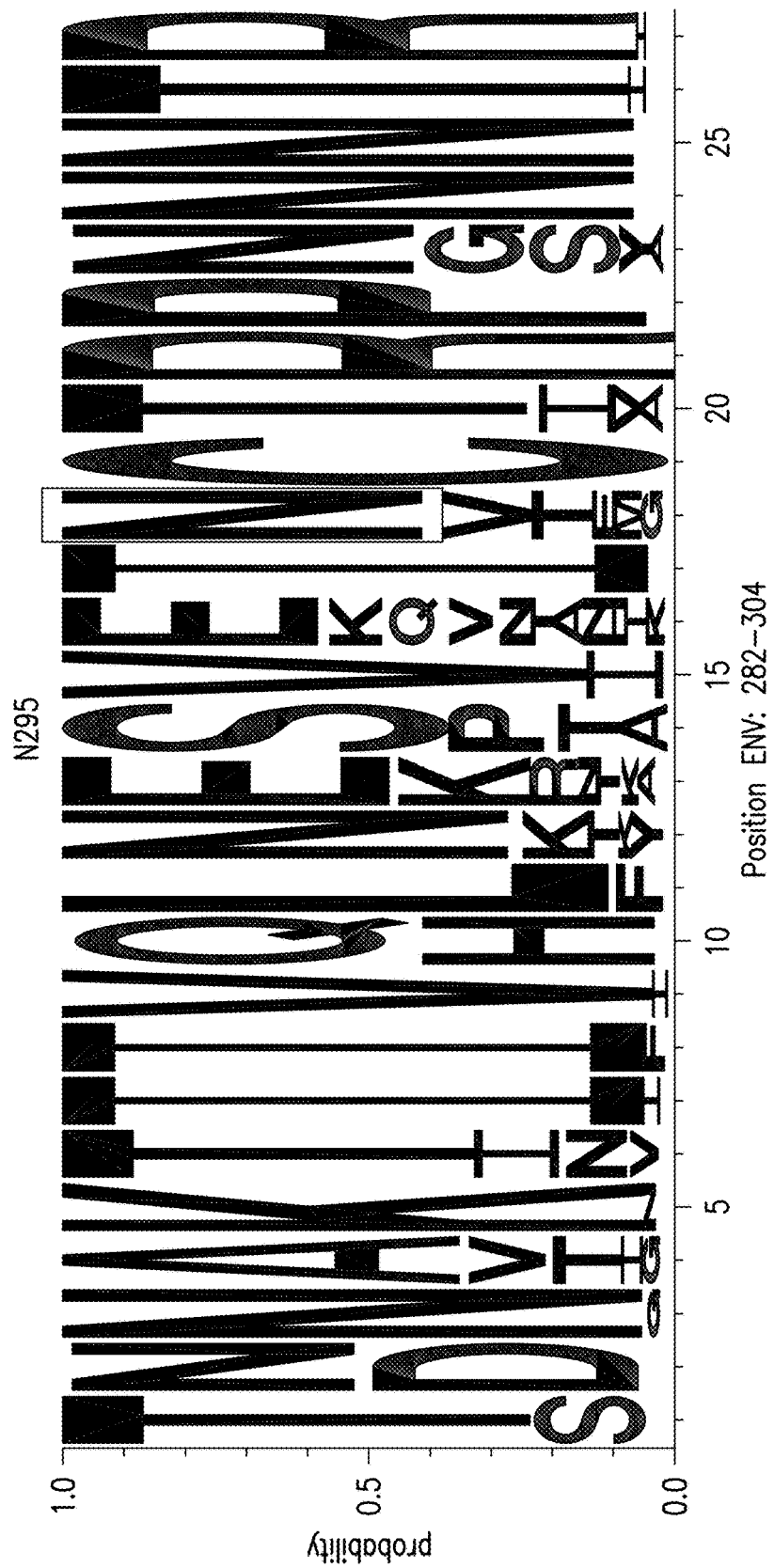
Figure 7C:
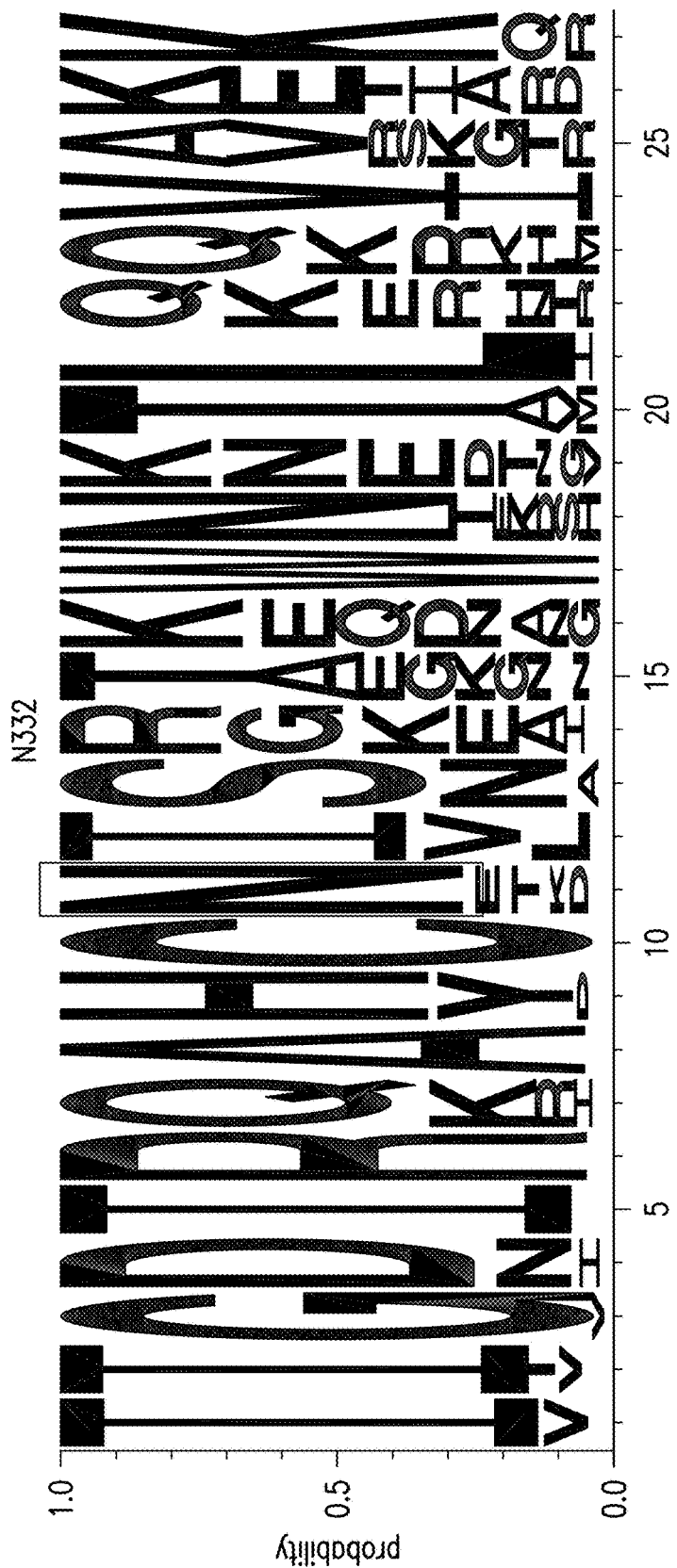
Figure 8A:
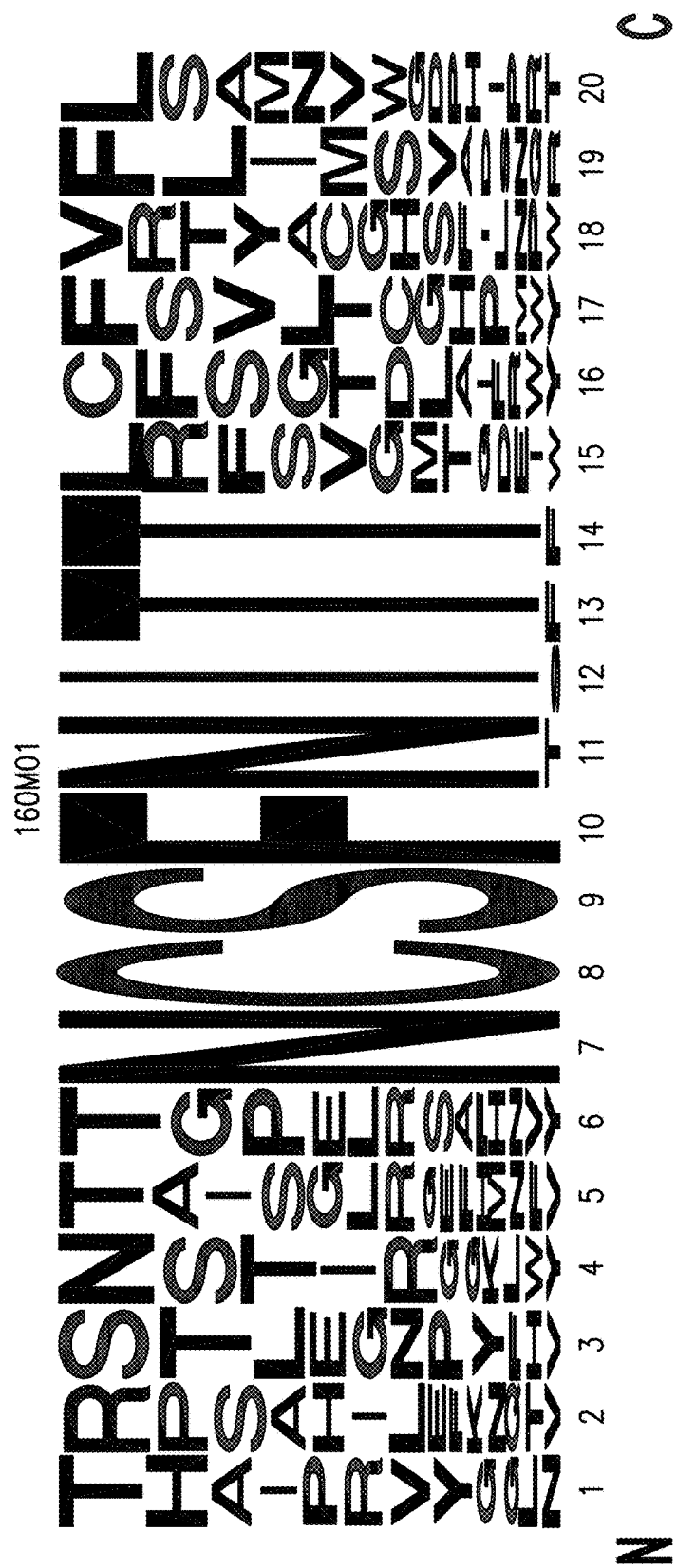
Figure 8B:
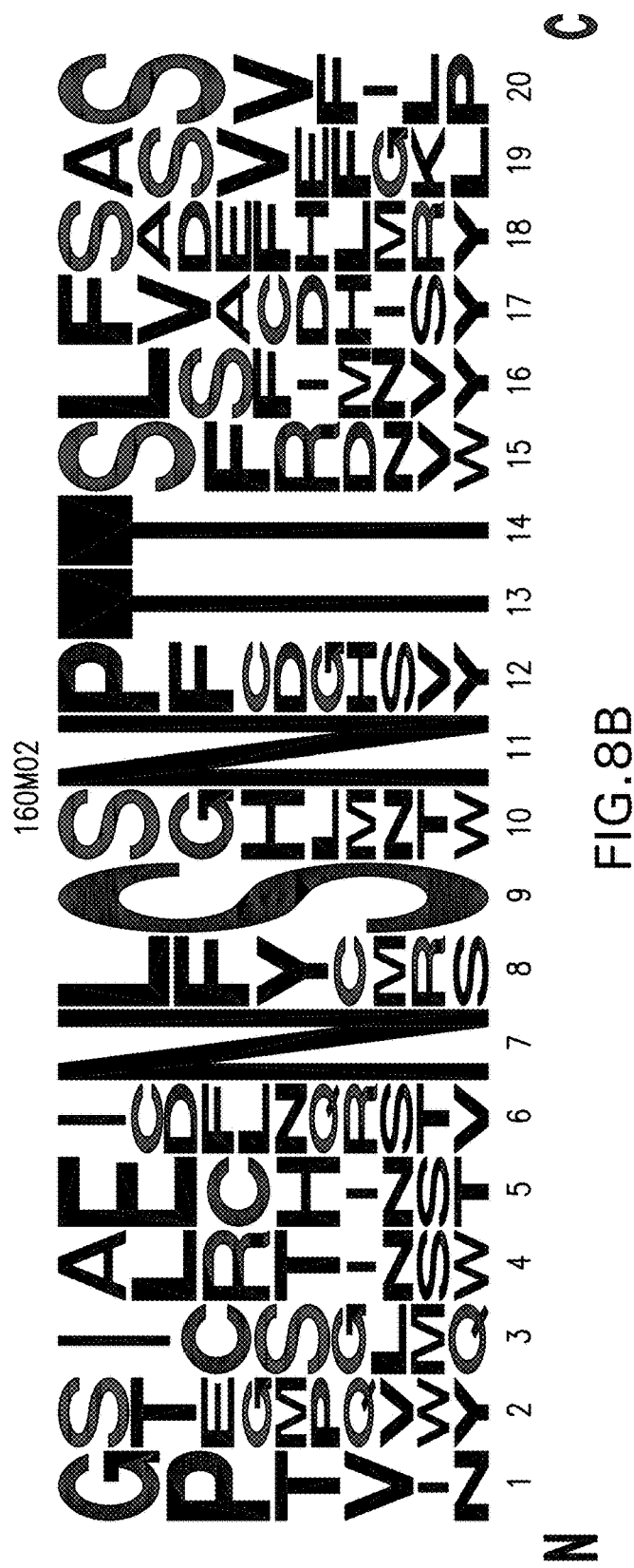
Figure 8C:
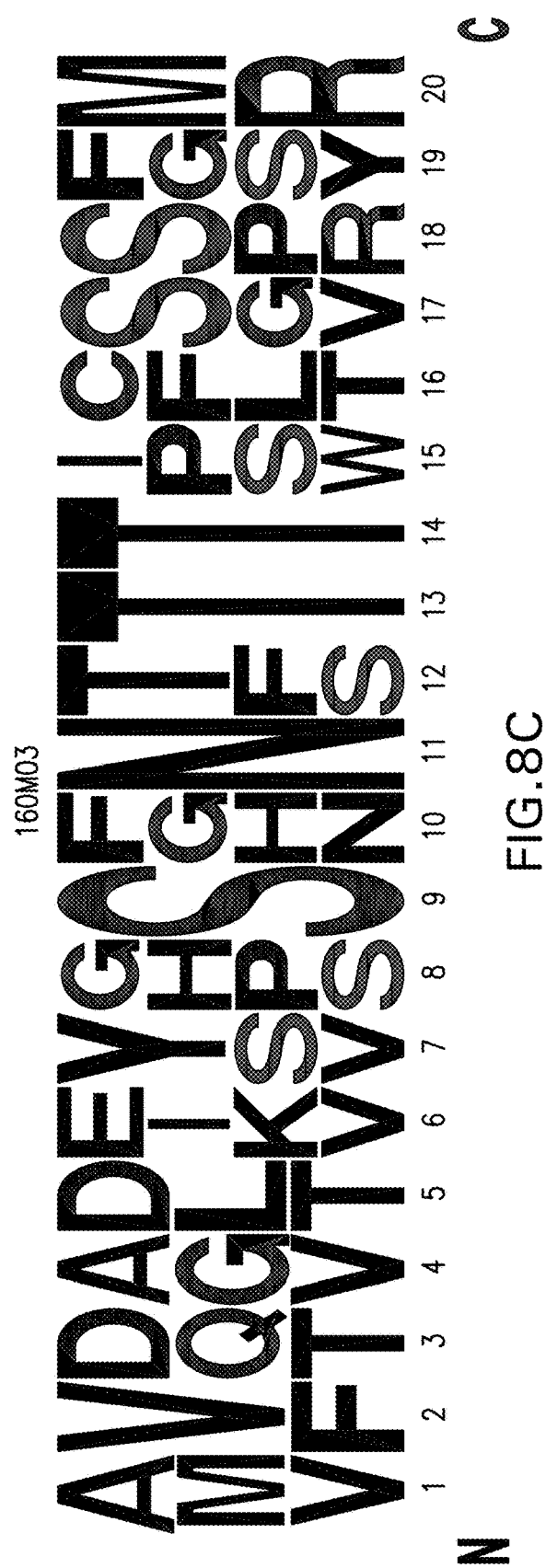
Figure 8D:
Figure 8E:
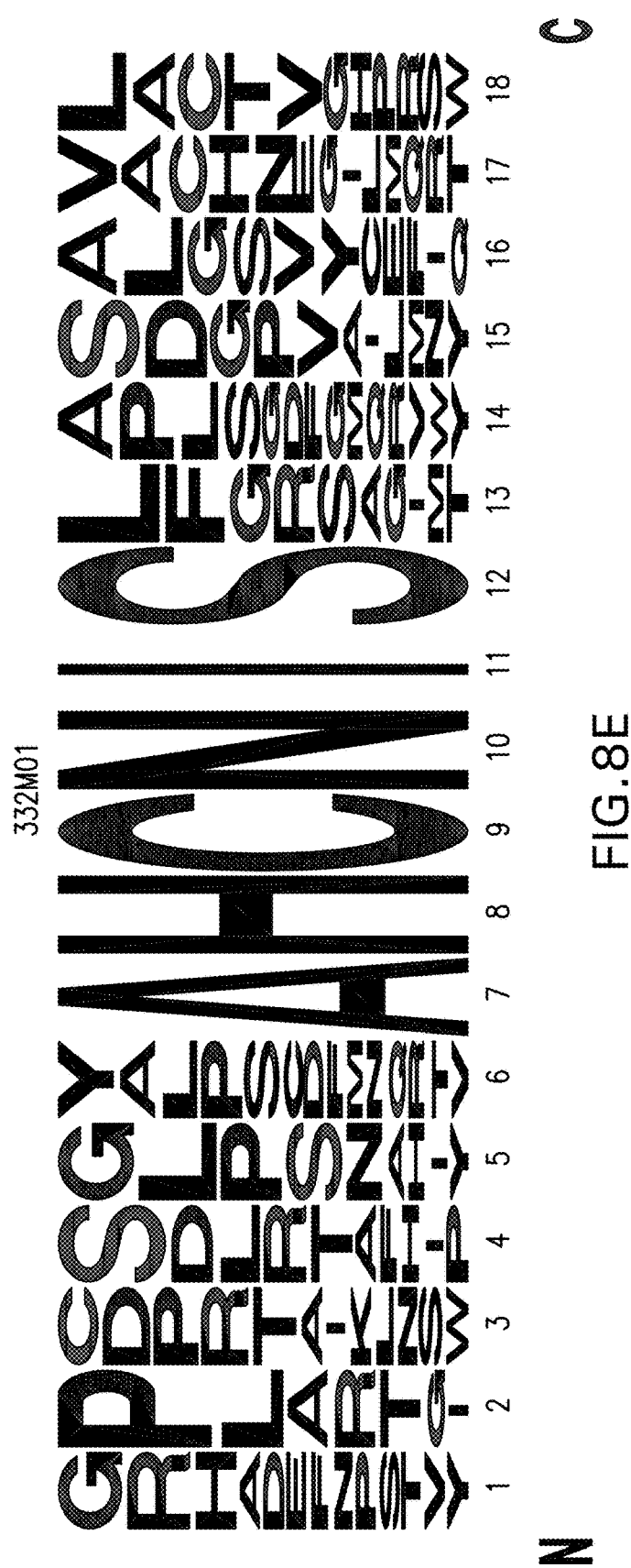

FIGS. 7A-D show the sequence analysis and motif sequences for the glyco-DNA motif plasmid constructs. In FIG. 7A-C, the different domains containing glycosylation domains of either N160 (FIG. 7A), N295 (FIG. 7B) or N332 (FIG. 7C) were aligned among 4633 sequences of HIV isolates from an HIV database. The Y axis stands for the conserved sequence rates, and the X axis depicts amino acid residues by location with the location number labeled according to HXB2 numbering. In FIG. 7D, the table is a summary of glyco-DNA motif constructs, each of which will serve to immunize a different group. The motif sequence listed is the sequence encoded by the motif gene which was inserted into the plasmid of PD1-P24 as for the PPMC plasmid described herein in accordance with one or more embodiments.

FIGS. 8A-F shows the sequence alignments of the six different glyco-DNA motif plasmids, as verified by sequencing. Each group of glyco-DNA motif plasmid libraries was sequenced for more than 60 clones, and the sequencing results of each library was aligned. The height of amino acid residues stands for the percent conservation of the residue that exist in the different clones.

Figure 9:
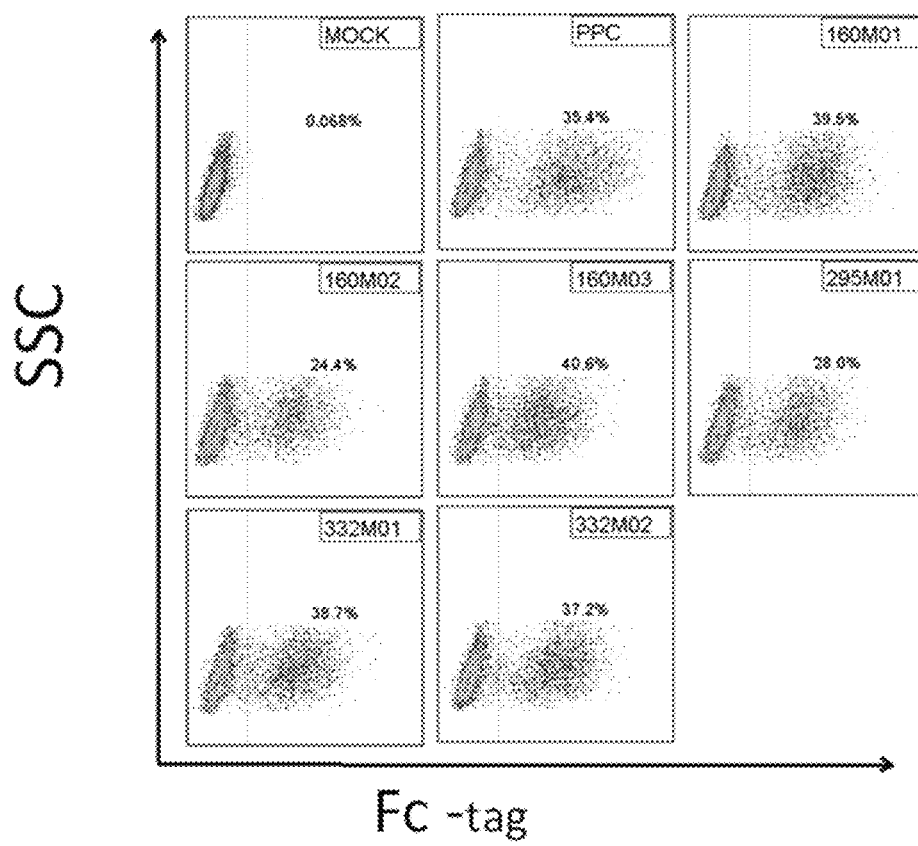

FIG. 9 shows FACS data of 293T cells transiently transfected with different plasmids as indicated. MOCK was taken as negative control without plasmid, and PPC was the background plasmid as positive control. Glyco-DNA motif plasmids 160M01, 160M02, 160M03, 295M01, 332M01, and 332M02 are newly constructed plasmids containing different glycosylation motifs as shown in FIGS. 8A-F.

Figure 10:
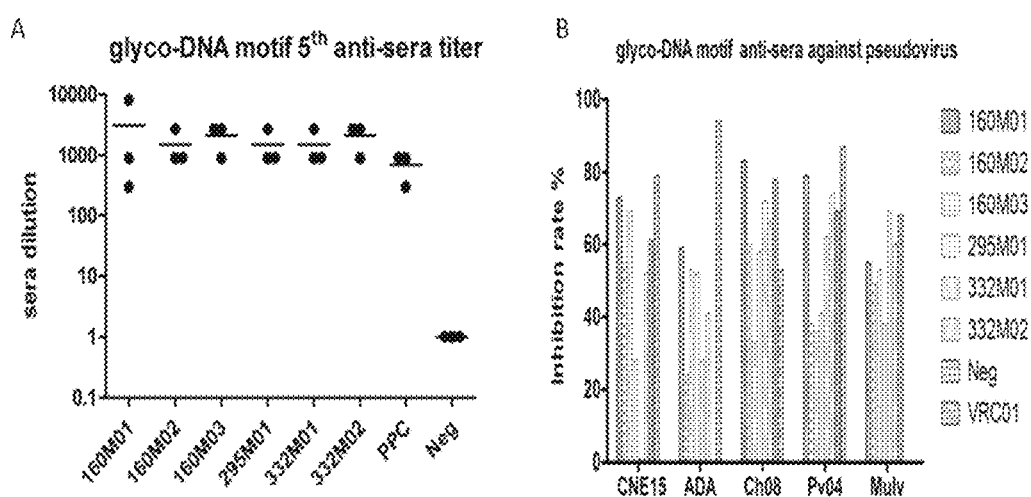

FIGS. 10A-B show the results of a neutralizing assay, in particular graphs showing the characterization of anti-sera titer and neutralization against different subtypes of HIV. In FIG. 10A, the titer of anti-sera against P24 was detected by ELISA. In FIG. 10B, anti-sera from different glyco-DNA motif immunizations were characterized by using pseudovirus neutralization against different subtypes of HIV. The negative control was anti-sera from PBS group, and VRC01 (a well-known neutralizing antibody) was used as a positive control. Mulv is a pseudovirus constituted by Murine Leukemia Virus envelope protein with gag-pol of PNL4-3 backbone, which was used as a negative virus.

FIGS. 11A-B are membrane blots or gels showing Anti-sera binding with gp120. Anti-sera binding with gp120 was characterized by western-blotting. For both gels, lanes 1, 3, 5, and 7 show gp120 protein of subtype IIIB, ADA, JR-FL, and SF162. For both gels, lanes 2, 4, 6, and 8 show the same four different subtypes gp120 in which the polysaccharide was removed by EndoH. FIG. 11A shows the membrane with transferred gp120 incubated with 160M01 anti-sera. FIG. 11B shows the membrane with transferred gp120 protein incubated with anti-sera from an HIV positive human patient.

Figure 12:
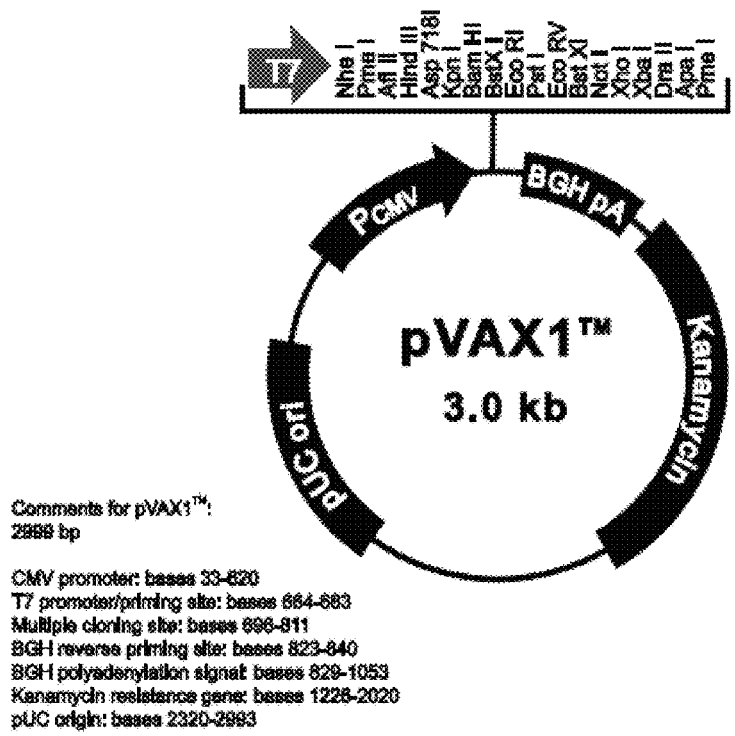

FIG. 12 shows key features and sequences of the pVAX-1 vector used in construction of the DNA motif plasmids described herein in accordance with one or more embodiments.

4.1 Definitions

Terms such as, "a", "an", or "one" as used herein generally mean "at least one", or "one or more" unless otherwise indicated. Further, the term "comprising" is intended to mean "including" and thus allows for the presence of other constituents, features, conditions, or steps than those explicitly recited.

The term "antibody" as used herein generally includes monoclonal and polyclonal antibodies. More specifically, the term "antibody" can also include full-length monoclonal antibodies, polyclonal antibodies, multispecific antibodies (e.g., bispecific antibodies), and antibody fragments, so long as they exhibit the desired biological activity, i.e. to function as described in the below detailed description.

The term "antigen" generally refers to a substance of matter that is recognized by the immune system's specifically recognized components (e.g., antibodies, T-cells).

The terms "broad neutralization", "broadly neutralizing" and the like, generally refer to an antibody (e.g., "broadly neutralizing antibodies [bNAb]) or sera that can neutralize more than one subtype of a virus.

The term "DNA motif vaccine" refers to a vaccine comprising a DNA molecule having a DNA sequence encoding a gene or genes for a specific motif amino acid residues, protein, peptide, or polypeptide, which produce the encoded motif amino acid residues, protein, peptide, or polypeptide in the vaccine recipient to trigger an immune response.

The term "epitope" generally refers to the region in an antigen or immunogen that is recognized by the immune system, such as by antibodies, B-cells, or T-cells. As used herein, an "epitope" typically refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence or stimulates a cellular immune response. The term "epitope" can encompass sequences identical to the native sequence, as well as modifications to the native sequence, such as deletions, additions and substitutions (generally conservative in nature). In certain embodiments, the antigens used in the invention may comprise only a single epitope, GPG.

"HIV" generally refers to human immunodeficiency virus 1 (HIV-1), unless otherwise indicated.

The term "immunogen" generally refers to a substance of matter that is capable of inducing an adaptive immune response in an individual, where said adaptive immune response targets the immunogen. In relation to the present application, an immunogen will induce antibodies that react with the immunogen. In other words, an immunogen can be an antigen that is capable of inducing immunity.

The terms "nucleic acid fragment" and "nucleic acid sequence" as used herein are understood as any nucleic acid molecule. The term includes nucleic acid molecules of any length e.g. from 10 to 10000 nucleotides, depending on the use. When the nucleic acid molecule is for use as a pharmaceutical, e.g. in DNA therapy, or for use in a method for producing a polypeptide according to the present disclosure, a molecule encoding at least one epitope is preferably used, having a length from about 3-10, 10-15, 15-18, 18-100, 100-200, 200-400, 400-1000 nucleotides, the molecule being optionally inserted into a vector.

The term "polypeptide" as used herein should have its usual meaning. That is an amino acid chain of any length, including a full-length protein, oligopeptides, short peptides and fragments thereof, wherein the amino acid residues are linked by covalent peptide bonds. The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a his-tag or a signal peptide. Each polypeptide may thus be characterized by specific amino acids and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". Each polypeptide is encoded by a specific nucleic acid sequence. It will be understood that such sequences include analogues and variants thereof wherein such nucleic acid sequences have been modified by substitution, insertion, addition or deletion of one or more nucleic acid. Substitutions are preferably silent substitutions in the codon usage which will not lead to any change in the amino acid sequence, but may be introduced to enhance the expression of the protein.

The term "therapeutic immunity" or a "therapeutic immune response" as used herein generally refers to immunity or eliciting an immune response against an infectious agent that ameliorates or eliminates an infection or reduces at least one symptom thereof.

The term "vaccine" generally refers to a composition comprising an immunogen and which is capable of inducing an immune response which is either capable of reducing the risk of developing a pathological condition or capable of inducing a therapeutically effective immune response which may aid in the cure of (or at least alleviate the symptoms of) a pathological condition.

5. DETAILED DESCRIPTION

There are two main reasons leading to the failure of a prophylactic AIDS vaccine. One is that the envelope protein of HIV-1 is highly mutated. Another is that the HIV-1 particle is heavily covered by polysaccharides.

The present application relates to a novel vaccine strategy, DNA motif immunization, which can generate antibodies directed to conserved domains and also to polysaccharide epitopes modified in vivo to elicit antibodies. As a proof of concept (POC) for DNA motif immunization, a DNA motif plasmid library, named PPMC, was constructed by introduction of random nucleotides flanking the two sides of a fixed targeted epitope. This fixed targeted epitope can encode an amino acid fragment ranging in length from 5-50 amino acid residues. This DNA motif plasmid library (PPMC), when used as an immunogen to inoculate mice, induced GPG-specific antibodies that neutralized 100% HIV-1 strains of various subtypes tested that contained the GPG motif in the V3 region. Additionally, six groups of DNA motif libraries containing a glycosylation motif (e.g., NXS/T) (referred to herein as glyco-DNA motif), were constructed. In particular, the 160M01 glyco-DNA motif plasmid vaccine induced antibodies specific for the polysaccharide of gp120.

An object of the present application is to construct a new form of DNA vaccine, called DNA motif vaccines. To this end, a series of primer libraries were synthesized to introduce the motif gene into the backbone of the pVAX backbone vector. Sequencing results and FACS data indicate that peptide motif construction can be reproduced in DNA motif plasmid via these methods using the primer combinations described herein (FIGS. 1A-B and FIG. 2). In addition, the glyco-DNA motif plasmids containing the coding gene of glycosylation were also constructed and confirmed via the same strategy (FIGS. 7A-D). Thus, two new techniques, one utilizing a form of regular DNA motif vaccine and another using the glyco-DNA motifs are established herein for eliciting the desired immune responses.

Another object of the present application is, accordingly, to provide a novel method of immunogen design for DNA motif vaccines capable of eliciting therapeutically significant antibodies against virus infection, such as, for example, HIV infection. Proof of concept of DNA motif immunization has been accomplished for the first time. Specifically, it is shown herein that PPMC, one of the DNA motif plasmids, can induce high titer antibodies against the native protein containing GPG epitope (FIG. 2). Additionally, a panel of HIV pseudoviral neutralization experiments were conducted, which indicate that the anti-sera induced by PPMC can neutralize various subtypes of HIV infections, which contain the GPG epitope in the tip of V3 loop.

Yet another object of the present application is to provide a DNA motif vaccine capable of inducing robust cellular immunity. After DNA motif immunization, PBMC and splenocytes were extracted to test the efficacy of cellular immunity. This data indicates that the PPMC group induced a high percentage of positive T cells specific for the CD8 epitope (FIG. 5), and elicited cells secreting IFN-γ upon additional of CD4 and CD8 epitope peptides (FIG. 6). These data illustrate that DNA motif vaccines described herein can induce robust cellular immunity.

Yet a further object of the present application is to provide a glyco-DNA motif vaccine capable of inducing antibodies specific for host-derived carbohydrates on a different protein, such as gp120 of HIV. After glyco-DNA motif immunization with the 160M01 plasmid, anti-sera were tested by western-blot for binding with different subtypes of gp120 and gp120. The results showed that anti-sera induced by 160M01 can bind specifically to native gp120 instead of gp20 without glycogen, indicating such anti-sera bind specifically to host-derived carbohydrates on gp120. Taken together, glyco-DNA motif can induce antibodies specific for host-derived carbohydrates.

A further object of the present application is to provide a DNA motif vaccine capable of eliciting production of therapeutically effective antibodies against conserved domain or host-derived carbohydrate epitopes and robust cellular immunity in patients suffering from viral infections. Constructed DNA motifs in the plasmids tested herein can induce broadly neutralizing antibodies against conserved domain and glycogen of HIV envelope protein and robust cellular immunity in the animal model.

Peptide motif immunization, as described in WO2013/040564, elicited NJU009 neutralizing antibodies to different subtypes of HIV-1; while a shortcoming of peptide immunization includes exhibiting a shorter half-life in contrast to protein immunization and DNA immunization, with DNA immunization exhibiting the longest half-life. Additionally, DNA immunization can elicit robust cellular immunity compared to peptide immunization. Moreover, DNA plasmid can be transfected in muscle cells to express and to be modified with polysaccharide if it contains the glycosylation motif in vivo during DNA immunization. The present results establish the platform of PD1 targeted DC cells for DNA immunization (PD1-P24, PPC) which can enhance immunity while eliciting cellular immunity against HIV-1 infection without the induction of bNAbs against HIV-1. Finally, further results as described herein illustrate the advantage of combining the peptide motif and DNA immunization of PD1 targeted DC cells to construct DNA motif immunization.

Here, a series of primer libraries were synthesized. In one or more embodiments, the motif gene was introduced into the backbone of PD1-P24 vector. The sequencing results and FACS data indicate that peptide motif construction can be reproduced in DNA motif plasmid via the present methods introducing the motif gene/primer library described herein. Proof of concept of DNA motif immunization was shown for the first time, proving that PPMC can also induce bNAbs specific for GPG epitope and robust cellular immunity. In addition, this method was used to construct a glyco-DNA motif, such as 160M01, to induce antibodies specific for native configuration of polysaccharide epitope. The HIV particle is heavily masked by polysaccharides, and thus there is an urgent need to develop neutralizing antibodies targeting the polysaccharides. For a regular antigen, like protein, it is easy to induce an antibody when immunizing an animal or human being with the injecting protein. However, since polysaccharides belong to T-cell independent antigens and suffer immunosuppression, its immunogenicity is weaker compared with a regular protein antigen (e.g., T-cell dependent antigen). In addition, it is very difficult to synthesized polysaccharides in vitro to make sure that its configuration is consistent with its configuration in vivo. To this end, there has not been an effective way to elicit antibodies specific for native configuration of the polysaccharide epitope. Therefore it is significant to introduce a new method, glyco-DNA motif, to elicit antibodies against native configuration of polysaccharides. As such, an urgent vaccine to induce antibodies against polysaccharides was needed. Our glyco-DNA motif immunization can induce antibodies specific for native configuration of polysaccharide epitope n. Further, our glyco-DNA motif is a significant advancement for vaccine design and for the introduction of antibodies against polysaccharides.

In one or more embodiments, the present application provides several advancements over the art. Firstly, we introduced a new form of motif antigen, DNA motif, which can reproduce the result of peptide motif with longer half-life. Secondly, DNA motif can elicit not only robust cellular immunity, but also bNAbs against HIV. Thirdly, glyco-DNA motif, another kind of DNA motif containing glycosylation motif sites, can be modified with polysaccharide in muscle cells and then the polysaccharide epitope with the native polysaccharide configuration can be presented to the immune system to induce antibodies specific for polysaccharides. Fourthly, DNA motif is a candidate as an HIV vaccine. It is believed that, DNA motif immunization will usher in a field of vaccine design and a new strategy of introduction antibodies against weak immunogenicity epitope and polysaccharide epitope with native configuration.

As disclosed herein, embodiments of the present application include a DNA motif vaccine, comprising at least one plasmid, wherein the plasmid comprises a motif gene encoding at least the amino acid sequence GPG. In one or more implementations, the plasmid induces broadly neutralizing antibodies (bNAbs) against HIV. In certain embodiments, the plasmid has a pVAX vector backbone. Further, in at least one embodiment, the motif gene is comprised within a plasmid selected from the group consisting of PD1-P24-pVAX, PD1-OVA-pVAX, and CTLA4-P24-pVAX.

In certain embodiments, the P24 and OVA can be expressed in vivo to provide the function of carrier protein for the induction of antibodies specific for the motif epitope. Additionally, in certain embodiments, the PD1 and/or CTLA4 enhance the immunity responses of the motif epitope by targeting dendritic cells.

In one or more embodiments, the plasmid can include a primer selected from the group consisting of:

```
Fc Forward
                                         (SEQ ID NO: 7)
5' (GGC CCCGGC NNB NNB NNB NNB NNB NNB

ATCCTGATGCAGTACATCAAGG) 3';

P24 backward
                                         (SEQ ID NO: 8)
5' (VNN VNN VNN VNN VNN VNN CTCGAGCGGCAAAACTCTTG)

3';
and

OVA backward
                                         (SEQ ID NO: 9)
5' (VNN VNN VNN VNN VNN VNN

CTCGAGCGGAGGGGAAACA) 3'.
```

In certain embodiments, the motif gene can encode a number of fixed amino acid residues of an epitope capable of being bound by an antibody. Further, in at least one embodiment, the motif gene can encode a motif peptide comprising a first plurality of fixed amino acid residues in the center of the motif sequence, and a second and third plurality of random amino acid residues in the regions flanking the first plurality.

In one or more embodiments, the length of fixed amino acid residues ranges from 3 to 30 amino acid residues in the center of the motif sequence. In certain embodiments, the length of fixed amino acid residues in the center of the motif sequences is 3 to 5 amino acid resides, 5 to 8 amino acid residues, 8 to 10 amino acid resides, 10 to 12 amino acid residues, 12 to 15 amino acid residues, 15 to 18 amino acid residues, 18 to 20 amino acid residues, 20 to 25 amino acid residues, or 25 to 30 amino acid residues. In some embodiments, the length of fixed amino acid residues in the center of the motif sequences is 5 to 30 amino acid residues, 8 to 30 amino acid resides, 10 to 30 amino acid residues, 12 to 30 amino acid residues, 15 to 30 amino acid residues, 18 to 30 amino acid residues, or 20 to 30 amino acid residues.

In one or more embodiments, the random amino acid residues range from 5-50 amino acid residues and are encoded by a nucleotide fragment ranging in length of from 15-150 nucleotides. In certain embodiments, the random amino acid residues are encoded by a nucleotide fragment with a length of 15 to 20 nucleotides, 20 to 30 nucleotides, 30 to 40 nucleotides, 40 to 50 nucleotides, 50 to 60 nucleotides, 60 to 70 nucleotides, 70 to 80 nucleotides, 80 to 90 nucleotides, 90 to 100 nucleotides, 100 to 110 nucleotides, 110 to 120 nucleotides, 120 to 130 nucleotides, 130 to 140 nucleotides, or 140 to 150 nucleotides. In some embodiments, the random amino acid residues are encoded by a nucleotide fragment with a length of 20 to 150 nucleotides, 30 to 150 nucleotides, 40 to 150 nucleotides, 50 to 150 nucleotides, 60 to 150 nucleotides, 70 to 150 nucleotides, 80 to 150 nucleotides, 90 to 150 nucleotides, 100 to 150 nucleotides, 110 to 150 nucleotides, 120 to 150 nucleotides, or 130 to 150 nucleotides.

The term "sequence identity" indicates a quantitative measure of the degree of homology between two amino acid sequences of equal length or between two nucleotide sequences of equal length. The two sequences to be compared must be aligned to best possible fit allowing the insertion of gaps or alternatively, truncation at the ends of the protein sequences. Sequence identity can alternatively be calculated by the BLAST program e.g. the BLASTP program (Pearson, 1988). In certain embodiments, alignment is performed with the sequence alignment method Clustal W with default parameters as described by Thompson J D, et al 1994. A minimum percentage of sequence identity is at least 80%, at least 85%, at least 90%, at least 91%, at least 92%, at least 93%, at least 94%, at least 95%, at least 96%, at least 97%, at least 98%, at least 99%, at least 99.5% and at least 99.9%.

In certain embodiments, the DNA encodes a motif that is a polypeptide. The polypeptide described herein comprises an immunogenic portion of the polypeptide, such as an epitope for a B-cell or T-cell. The immunogenic portion of a polypeptide is a part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. In certain embodiments, the peptides have a length of e.g. 8 to 11 amino acid residues derived from the polypeptide. In certain embodiments, the polypeptide has a length of at least 7 amino acid residues, such as at least 8, at least 9, at least 10, at least 12, at least 14, at least 16, at least 18, at least 20, at least 22, at least 24, and at least 30 amino acid residues. In certain embodiment, the polypeptide has at most 50, 40, 35, 30, 25, and 20 amino acid residues. In certain embodiments, the polypeptides are 18, such as 17, 16, 15, 14, 13, 12 and even 11 amino acid residues. In certain embodiments, the polypeptides are 7-12 amino acid residues. In certain embodiments, the polypeptides are 11, 10, 9, 8, 7, 6, 5, 4, 3 amino acid residues.

A common feature of the polypeptides disclosed herein is their capability to induce an immunological response as illustrated in the examples. It is understood that a variant of a polypeptide described herein produced by substitution, insertion, addition or deletion may also be immunogenic as determined by any of the assays described herein.

In yet additional embodiments, the motif gene can comprise a glycosylation motif gene encoding the motif peptide NxS/T. In at least one embodiment, the glycosylation motif peptide NxS/T is optionally modified to add host-derived carbohydrates on the amino acid residue of Asparagine (N) for facilitating in vivo peptide expression.

In one or more embodiments, the DNA motif vaccine (glyco-DNA motif vaccine) can induce antibodies specific for host-derived carbohydrates. In yet additional embodiments, the DNA motif vaccine is capable of inducing antibodies against a glycogen epitope to inhibit viral or bacterial infections, including HIV infection.

In certain embodiments, the glycosylation motif gene is inserted within the PD1-P24-pVAX plasmid. In at least one embodiment, the glyco-DNA motif vaccine comprises one of more of the plasmids selected from the group consisting of 160M01, 160M02, 160M03, 295M01, 332M01, and 332M02.

In certain embodiments, the plasmid includes a primer selected from the group consisting of:

```
                                         (SEQ ID NO: 13)
AACTGCTCCTTCAACATCACCACCNNBNNBNNBNNBNNBNNBATCCTGAT

GCAGTACATCAAGG;

(SEQ ID NO: 14)
AACNNBTCCNNBAACNNBACCACCNNBNNBNNBNNBNNBNNBATCCTGAT

GCAGTACATCAAGG;

(SEQ ID NO: 15)
NNBNNBTCCNNBAACNNBACCACCNNBNNBNNBNNBNNBATCCTGAT

GCAGTACATCAAGG;

(SEQ ID NO: 16)
ATCAACTGCACCCGCCCCNNBNNBNNBNNBNNBNNBATCCTGATGCAGTA

CATCAAGG;

(SEQ ID NO: 17)
GCCCACTGCAACATCTCCNNBNNBNNBNNBNNBNNBATCCTGATGCAGTA

CATCAAGG;

(SEQ ID NO: 18)
GCCNNBTGCAACNNBTCCNNBNNBNNBNNBNNBNNBATCCTGATGCAGTA

CATCAAGG;
and
                                         (SEQ ID NO: 19)
VNN VNN VNN VNN VNN VNN CTCGAGCGGAGGGGAAACA.
```

In at least one embodiment, the glyco-DNA motif vaccine comprises the plasmid 160M01. In certain embodiments, the plasmid 160M01 can be constructed by inserting the motif gene coding the glycosylation peptide of N160 in HIV gp120. In yet additional embodiments, the DNA motif vaccine can induce antibodies specific for glycogen of gp120.

Embodiments of the present application can further include a method of inhibiting HIV-1 infection comprising administering one or more of the DNA motif plasmid vaccines or glycosylation motif gene (glyco-DNA) plasmid vaccines described herein to a patient in need thereof.

In yet additional embodiments, the glyco-DNA motif vaccine can further comprise at least one motif peptide selected from the group consisting of xxxxxNCSFNIT-Txxxx (SEQ ID NO: 1), xxxxxNxSxNxTTxxxx (SEQ ID NO: 2), xxxxxxxSxNxTTxxxx (SEQ ID NO: 3), xxxxxINC-TRPxxxxx (SEQ ID NO: 4), xxxxxAHCNISxxxxx (SEQ ID NO: 5), and xxxxxAxCNxSxxxxx (SEQ ID NO: 6).

Embodiments of the present application can also include a method of inducing a cellular and humoral immune response in a patient comprising administering one or more of the DNA motif vaccine alone, or in combination with one or more glycosylation motif gene plasmid vaccines described herein to a patient in need thereof.

Embodiments of the present application can further include a method of DNA motif immunization comprising immunizing an animal model or human subject with one or more of the DNA motif vaccines alone, or in combination with one or more glycosylation motif gene plasmid vaccines described herein.

At least one embodiment of the present application includes methods for generating a plasmid library comprising any combination of the primers described herein for making a DNA motif vaccine plasmid described herein.

5.1 Antibodies and Vaccines

In one or more embodiments, the present application provides antibodies to bind to HIV-1 gp120, as described above. The term 'antibody' is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term 'monoclonal antibody' as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier 'monoclonal' indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody as described herein. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations can be advantageous in that they are typically uncontaminated by other immunoglobulins.

The modifier 'monoclonal' indicates the character of the antibody as being obtained from a substantially homogeneous population of antibodies, and is not to be construed as requiring production of the antibody by any particular method. For example, the monoclonal antibodies to be used in accordance with the present application may be made by a variety of techniques, including, but not limited to, recombinant DNA methods, phage-display technologies, and the hybridoma method.

The monoclonal antibodies herein specifically include 'chimeric' antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

A 'human antibody' is one which possesses an amino acid sequence which corresponds to that of an antibody produced by a human and/or has been made using any of the techniques for making human antibodies as disclosed herein. Human antibodies can be produced using various techniques known in the art, including phage-display libraries. Human antibodies can also be prepared by administering the antigen to a transgenic animal that has been modified to produce such antibodies in response to antigenic challenge, but whose endogenous loci have been disabled.

A vaccine is a biological preparation that establishes or improves immunity to a particular disease. Vaccines can be prophylactic (e.g. to prevent or ameliorate the effects of a future infection by any natural or "wild" pathogen), post-exposure (e.g. to prevent reactivation in latently infected individuals without clinical symptoms) or therapeutic (e.g. vaccines used to treat active disease either alone or combined with antibiotic treatment to shorten treatment).

The nucleic acid fragments encoding a motif described herein may be used for effecting in vivo expression of antigens, i.e. the nucleic acid fragments may be used in so-called "DNA motif vaccines". Hence, one or more embodiments can also relates to a post exposure vaccine comprising a nucleic acid fragment, the vaccine effecting in vivo expression of antigen by an animal, including a human being, to whom the vaccine has been administered, the amount of expressed antigen being effective to confer treatment of the infections in an animal, including a human being.

DNA motif vaccines can cause both cell mediated immune responses and antibody responses. Accordingly, DNA motif vaccines represent an attractive alternative to other modes of vaccination.

5.2 Compositions and Formulations

The vaccines and/or antibodies of the present application may be formulated into a pharmaceutical form, preferably in combination with a pharmaceutically acceptable carrier. The pharmaceutical forms suitable for injectable use include sterile aqueous solutions or dispersions and sterile powders for the extemporaneous preparation of sterile injectable solutions or dispersions. In all cases for injectable use, the form must be sterile and must be fluid to the extent that syringability exists. It must be stable under the conditions of manufacture and storage and must be preserved against contamination with microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of contamination with microorganisms can be brought about by various antibacterial and antifungal agents, for example, parabens, chlorobutanol, phenol, sorbic acid, thimerosal, and the like. In certain embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

In certain embodiments, the composition according to the present disclosure comprises immunogenic delivery systems that is plasmids expressing a motif protein (or proteins) or peptide (or polypeptides).

For parenteral administration in an aqueous solution, for example, the solution should be suitably buffered if necessary and the liquid diluent first rendered isotonic with sufficient saline or glucose. These particular aqueous solutions can be especially suitable for intravenous, intraarterial, intramuscular, subcutaneous, intratumoral and intraperitoneal administration. In this connection, sterile aqueous media that can be employed is known to those of ordinary skill in the art in light of the present application. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Sterile injectable solutions can be prepared by incorporating the active compounds in the required amount in the appropriate solvent with various of the other ingredients enumerated above, as required, followed by filtered sterilization. Generally, dispersions can be prepared by incorporating the various sterilized active ingredients into a sterile vehicle which contains the basic dispersion medium and the required other ingredients from those enumerated above. In the case of sterile powders for the preparation of sterile injectable solutions, preferred methods of preparation include vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts and which can be formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations can be administered in a variety of dosage forms such as injectable solutions, drug release capsules and the like.

As used herein, 'carrier' includes, but is not limited to, solvents, dispersion media, vehicles, coatings, diluents, antibacterial and antifungal agents, isotonic- and absorption-delaying agents, buffers, carrier solutions, suspensions, colloids, liposomes and virosomes. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase 'pharmaceutically-acceptable' or 'pharmacologically-acceptable' refers to molecular entities and compositions that do not produce an allergic or similar untoward reaction when administered to a human. The preparation of an aqueous composition that contains a protein as an active ingredient is well understood in the art. Typically, such compositions can be prepared as injectables, either as liquid solutions or suspensions. Solid forms suitable for solution in, or suspension in, liquid prior to injection can also be prepared.

The vaccine composition can also contain an agent that enhances the protective efficacy of the vaccine, such as an adjuvant. Adjuvants include any compound or compounds that act to increase a protective immune response to the peptide antigen, thereby reducing the quantity of antigen necessary in the vaccine, and/or the frequency of administration necessary to generate a protective immune response. Adjuvants can include for example, emulsifiers; muramyl dipeptides; pyridine; aqueous adjuvants such as aluminum hydroxide; oxygen-containing metal salts; chitosan-based adjuvants, and any of the various saponins, oils, and other substances known in the art, such as Ampfaigen, LPS, bacterial cell wall extracts, bacterial DNA, CpG sequences, synthetic oligonucleotides and combinations thereof, *Mycohacterialplilei* (*phlei*) cell wall extract (CWE), *M. phlei* DNA (M-D A), and M-DNA-*M phlei* cell wall complex (MCC), heat-labile enterotoxin (LT), cholera toxin (CT), and cholera toxin B subunit (CTB). Compounds which can serve as emulsifiers include natural and synthetic emulsifying agents, as well as anionic, cationic and nonionic compounds. Oxygen-containing metal salts include salts of Al, K, Ca, Mg, Zn, Ba, Na, Li, B, Be, Fe, Si, Co, Cu, Ni, Ag, Au, and Cr which are sulfates, hydroxides, phosphates, nitrates, iodates, bromates, carbonates, hydrates, acetates, citrates, oxalates, and tartrates, and mixed forms thereof, including aluminum hydroxide, aluminum phosphate, aluminum sulfate, potassium aluminum sulfate, calcium phosphate, Maalox (mixture of aluminum hydroxide and magnesium hydroxide), beryllium hydroxide, zinc hydroxide, zinc carbonate, zinc chloride, and barium sulfate. Among the synthetic compounds, anionic emulsifying agents can include, for example, the potassium, sodium and ammonium sails of lauric and oleic acid, the calcium, magnesium and aluminum salts of fatty acids, and organic sulfonates such as sodium lauryl sulfate. Synthetic cationic agents include, for example, cetyltrhethylammonlum bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan. monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's incomplete Adjuvant (FIA) are two common adjuvants that are commonly used in vaccine preparations, and are also suitable for use in accordance with one or more embodiments of the present application. Both FCA and FIA are water-in-mineral oil emulsions; however, FCA also contains a killed *Mycobacterium* sp. Adjuvants for mucosal vaccines can include galactosyl ceramide (GalCer).

Immunomodulatory cytokines can also be used in the vaccine compositions to enhance vaccine efficacy, for example, as an adjuvant. Non-limiting examples of such cytokines include interferon alpha (IFN-a), interleukin-2 (IL-2), and granulocyte macrophage-colony stimulating factor (GM-CSF), or combinations thereof.

In certain embodiments, it may be advantageous to combine or include within the compositions additional polypeptides, peptides or polynucleotides encoding one or more polypeptides or peptides that function as "co-stimulatory" component(s). Such co-stimulatory components may include, for example, cell surface proteins, cytokines or chemokines in a composition of the present application. The co-stimulatory component may be included in the composition as a polypeptide or peptide, or as a polynucleotide encoding the polypeptide or peptide, for example.

When provided prophylactically, the immunogenic compositions of the present application can be administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and can be advantageously used as soon after infection as possible, preferably before appearance of any symptoms of AIDS but may also be used at (or after) the onset of the disease symptoms.

5.3 Dosage

DNA motif vaccine compositions of the invention are typically administered to a subject in an amount sufficient to provide a benefit to the subject. This amount is defined as a "therapeutically effective amount." The therapeutically effective amount will be determined by the efficacy or potency of the particular composition, the duration or frequency of administration, and the size and condition of the subject, including that subject's particular treatment response. Additionally, the route of administration should be considered when determining the therapeutically effective amount. It is anticipated that the therapeutically effective amount of a DNA motif vaccine composition of the invention will range from about 0.1 μg/kg to 1 mg/kg of total nucleic acid. Suitable doses include from about 5 μg/kg-500 mg/kg of total DNA, 10 μg/kg-250 μg/kg of total DNA, or 10 μg/kg-170 μg/kg of total DNA. In one embodiment, a human subject (18-50 years of age, 45-75 kg) is administered 1.2 mg-7.2 mg of DNA. "Total DNA" and 'total nucleic acid" refers to a pool of nucleic acids encoding distinct immunogenic molecules. For example, a dose of 50 mg of total DNA encoding 5 different immunogenic molecules can have 1 mg of each molecule. DNA motif vaccines may be administered multiple times, such as between about 2-6 times. In an exemplary method, 100 μg of a DNA composition is administered to a human subject at 0, 4, and 12 weeks (100 μg per administration).

The treatments of the present application may include various 'unit doses.' A unit dose is defined as containing a predetermined-quantity of the therapeutic composition of the present application. The quantity to be administered, and the particular route and formulation, are within the skill of those in the clinical arts. A unit dose need not be administered as a single injection but may comprise continuous infusion over a set period of time. A unit dose may contain at least 0.01, 0.05, 0.1, 0.5, 1.0, 2.5, 5.0, 10.0, 15.0, 25.0 or 50.0 mg of the active ingredient. Optionally, a unit dose contains less than 0.01, 0.05, 0.1, 0.5, 1.0, 2.5, 5.0, 10.0, 15.0, 25.0 or 50.0 mg of the active ingredient. In at least one embodiment, a unit dose contains from about 0.001 mg to about 50 mg of the active ingredient. In one or more embodiments, a unit dose contains from about 1 mg to about 10 mg of active ingredient.

5.4 Methods of Administration

Administration can be via a parenteral or non-parenteral route. Routes of administration can vary with the nature of the disease, and include, e.g. intravenous, intrarterial, intradermal, transdermal, intramuscular, mucosal subcutaneous, percutaneous, intratracheal, intraperitoneal, perfusion and lavage. In one or more embodiments, administration is via a mucosal route, for example via a nasal, oral (via the mucosa of the digestive system), vaginal, buccal, rectal, sublingual, ocular, urinal, pulmonal or otolar (vie the ear) route. For nasal administration, an exemplary formulation can be a nasal spray, lavage, drop or squirt system.

In at least one embodiment, the vaccine composition can be administered in a single daily dose, or the total daily dosage may be administered in divided doses, for example, two, three or four times daily. Furthermore, the vaccine composition can be administered in intranasal form via topical use of suitable intranasal vehicles, via transdermal routes, using those forms of transdermal skin patches known to persons having ordinary skill in the art, by implantable pumps; or by any other suitable means of administration. To be administered in the form of a transdermal delivery system, for example, the dosage administration will be continuous rather than intermittent throughout the dosage regimen.

The dosage regimen utilizing the vaccine composition can be selected in accordance with a variety of factors including but not limited to type, species, age, weight, sex and medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter or arrest the progress of the disease or disorder that is being treated.

Vaccine administration may further comprise a prime-boost regimen. In these methods, one or more priming immunizations can be followed by one or more boosting immunizations. The actual immunogenic composition can be the same or different for each immunization and the type of immunogenic composition, the route, and formulation of the immunogens can also be varied. For instance, one useful prime-boost regimen provides for two priming immunizations, four weeks apart, followed by two boosting immunizations at 4 and 8 weeks after the last priming immunization. In one or more embodiments, either the prime or the boost, or both, may be administered in the form of a DNA molecule encoding the peptide or polypeptide in question.

Immunization schedules (or regimens) are well known and can be readily determined for the particular subject and immunogenic composition. As such, the immunogens can be administered one or more times to the subject. In one or more embodiments, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In one or more embodiments of the present application, the interval is longer, such as about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks.

The immunization regimes typically have from 1 to 6 administrations of the immunogenic composition, but may have as few as 1, 2, 3, 4 or 5. The methods of inducing an immune response can also include administration of an adjuvant with the immunogens. In some instances, annual, biannual or other long interval (5-10 years) booster immunization can supplement the initial immunization protocol.

At least one embodiment of the present application provides methods of inducing an immune response against HIV in a subject by administering an immunogenic composition of the present application. Such immunizations can be repeated multiple times at time intervals of at least 2, 4 or 6 weeks (or more), for example, in accordance with a desired immunization regime.

The immunogenic compositions of the present application can be administered alone, or can be co-administered, or sequentially administered, with other HIV immunogens and/or HIV immunogenic compositions, e.g., with 'other' immunological, antigenic or vaccine or therapeutic compositions thereby providing multivalent or combination compositions of the present application. Again, the ingredients and manner (sequential or co-administration) of administration, as well as dosages can be determined taking into consideration such factors as the age, sex, weight, species and condition of the particular subject, and the route of administration. When used in combination, the other HIV immunogens can be administered at the same time or at different times as part of an overall immunization regime, e.g., as part of a prime-boost regimen or other immunization protocol.

Other agents that may be utilized in conjunction with the compositions and methods provided herein include anti-HIV agents including, for example, protease inhibitor, an HIV entry inhibitor, a reverse transcriptase inhibitor, and/or or an anti-retroviral nucleoside analog. Suitable compounds can include, for example, Agenerase (amprenavir), Combivir (Retrovir/Epivir), Crixivan (indinavir), Emtriva (emtricitabine), Epivir (3tc/lamivudine), Epzicom, Fortovase/Invirase (saquinavir), Fuzeon (enfuvirtide), Hivid (ddc/zalcitabine), Kaletra (lopinavir), Lexiva (Fosamprenavir), Norvir (ritonavir), Rescriptor (delavirdine), Retrovir/AZT (zidovudine), Reyatax (atazanavir, BMS-232632), Sustiva (efavirenz), Trizivir (abacavir/zidovudine/lamivudine), Truvada (Emtricitabine/Tenofovir DF), Videx (ddI/didanosine), Videx EC (ddI, didanosine), Viracept (nevirapine), Viread (tenofovir disoproxil fumarate), Zerit (d4T/stavudine), and Ziagen (abacavir). Other suitable agents are known to those of skill in the art. Such agents may either be used prior to, during, or after administration of the compositions and/or use of the methods described herein.

Ribozyme therapy is also a choice for HIV/AIDS therapy. It uses engineered trans-cleaving ribozymes to cleave specific sequences by mutation of the substrate recognition sequences flanking the cleavage site sequence, and thus can be utilized to remove HIV gene such as U5, pol from the genome to achieve HIV replication inhibition. In one embodiment, the DNA motif vaccine composition provided herein is administered in combination with one or more engineered trans-cleaving ribozymes, or vectors expressing the trans-cleaving ribozymes, for HIV/AIDS treatment.

RNA-based anti-HIV gene genetic therapies are also among the various HIV/AIDS treatments, which inhibit viral replication via RNA interference. Anti-HIV gene siRNA (small interference RNA) or shRNA (short hairpin) may be engineered for sequence specific mRNA degradation. In addition, long antisense oligonucleotides may be designed to bind to mRNA of a HIV gene and trigger degradation of mRNA through an RNase H dependent pathway or block ribosome binding, and thus inhibiting gene expression. The HIV gene may be targeted include but not limited to HIV env, U1 and trans-activation response (TAR) elements. In one embodiment, the DNA motif vaccine composition provided herein is administered in combination with one or more anti-HIV gene molecules, or vectors expressing the antisense RNAs, for HIV/AIDS treatment.

Further, aptamers may be used for HIV/AIDS treatment as well. Aptamers are single-stranded RNA or DNA molecules that can bind proteins with high affinity as a decoy. These molecules, normally 15 to 40 bases long, can be used as decoys to bind viral proteins or as vehicles for targeted delivery of siRNAs. A lentiviral vector may be used to express such aptamer, which targets TAR and other viral protein key to virus replication. In one embodiment, the DNA motif vaccine composition provided herein is administered in combination with one or more aptamers, or aptamer expressing vectors, for HIV/AIDS treatment.

As discussed herein, 'treatment' includes both therapeutic treatment and prophylactic or preventative treatment, wherein the object is to prevent or slow down the targeted pathologic condition or disorder. Those in need of treatment include those already with the disorder as well as those prone to have the disorder or those in whom the disorder is to be prevented. The terms 'therapy', 'therapeutic', 'treatment' or 'treating' include the ability or action of reducing, alleviating or inhibiting or eliminating the symptoms or progress of a disease. Desirable effects of treatment include preventing occurrence or recurrence of disease, alleviation of symptoms, diminishment of direct or indirect pathological consequences of the disease, preventing metastasis, decreasing the rate of disease progression, amelioration or palliation of the disease state, and remission or improved prognosis. In some embodiments, methods and compositions of the present application are used to delay development of a disease or disorder or to slow the progression of a disease or disorder.

Treatment in accordance with the present application can include a method of treating a cancer or other neoplastic disorder which comprises administering to a patient in need of treatment a peptide, nucleic acid, antibody composition of the present application. In at least one embodiment, the treatment further comprises administering to said patient a chemotherapeutic drug, such as a drug in prodrug form. The two components may be administered together, for example in the form of a combined pill, or separately. Administration may also be sequential or simultaneous. 'Sequential' administration indicates that the components are administered at different times or time points, which may nonetheless be overlapping. Simultaneous administration indicates that the components are administered at the same time.

An effective amount, or preferably a therapeutically effective amount of the treatment of the present application is administered. An "effective amount" refers to an amount effective, at dosages and for periods of time necessary, to achieve the desired therapeutic or prophylactic result. The effective amount may vary according to the drug or prodrug with which the treatment is co-administered. A "therapeutically effective amount" of a treatment of the present application may vary according to factors such as the disease state, age, sex, and weight of the individual, and the ability of the protein, to elicit a desired therapeutic result. A therapeutically effective amount encompasses an amount in which any toxic or detrimental effects of the protein are outweighed by the therapeutically beneficial effects. A therapeutically effective amount also encompasses an amount sufficient to confer benefit, e.g., clinical benefit.

5.5 Kits

The present invention provides articles of manufacture and kits containing materials useful for treating the conditions described herein. The article of manufacture may include a container of a compound as described herein with a label. Suitable containers include, for example, bottles, vials, and test tubes. The containers may be formed from a variety of materials such as glass or plastic. The container holds a composition having a DNA motif vaccine which is effective for treating or preventing HIV infection. The label on the container may indicate that the composition is useful for treating specific conditions and may also indicate directions for administration.

In one or more embodiments, the present invention can provide for a kit for inducing bNAbs against HIV, the kit comprising a therapeutically effective amount of DNA motif vaccine and/or glyco-DNA motif vaccine. It is to be understood that any of the embodiments of the DNA motif vaccine and/or glyco-DNA motif vaccine can be included in one or more kits in accordance with one or more implementations of the present invention.

6. EXAMPLES

6.1 Methods 6.1.1 Construction of sPD1-Based Motif Vaccine and Controls

In accordance with one or more embodiments, three groups of DNA motif plasmid libraries were constructed: PPMC, POMC and CPMC in a background of the vector pVAX1, respectively. The pVAX1 vector was purchased from Invitrogen (Catalogue No. V260-20; Eugene, Oreg.). pVAX1 is a 3.0 kb plasmid vector designed for use in the development of DNA motif vaccines. The vector was constructed to be consistent with the Food and Drug Administration's (FDA) document: "Points to Consider on Plasmid DNA Vaccines for Preventive Infectious Disease Indications," published Dec. 22, 1996.

The coding sequences for the extracellular domains of murinePD1 (sPD1), CTLA4, HIV-1p24 fragments and ovalbumin were previously introduced in the backbone of pVAX1 to construct the plasmids: PD1-P24-Fc, PD1-OVA-Fc and CTLA4-P24-Fc. (See, Zhou, Cheung et al. 2013). All plasmids contained a rabbit Fc tag to facilitate protein purification.

In order to insert the DNA encoding the motif target sequence into the desired plasmid, three primers were synthesized;

```
The primer 01 Fc Forward
                                      (SEQ ID NO: 7)
5' (GGC CCCGGC NNB NNB NNB NNB NNB

NNBATCCTGATGCAGTACATCAAGG) 3'
```

-continued
```
The primer 02 P24 backward
                                      (SEQ ID NO: 8)
5' (VNN VNN VNN VNN VNN VNN

CTCGAGCGGCAAAACTCTTG) 3'

The primer 03 OVA backward
                                      (SEQ ID NO: 9)
5' (VNN VNN VNN VNN VNN VNN

CTCGAGCGGAGGGGAAACA) 3'
``` wherein V indicates the nucleic acid can be either A, C or G; where N indicates that the nucleic acid can be either A, C, G, or T; B indicates that the nucleic acid can be either C or G or T; and wherein VNN indicates the random combination of the above nucleotides which could encode variable amino acid residues.

The underlined primer sequences are sequences complementary to the plasmid backbone; the left part of primer sequence without underlining corresponds to the inserted gene encoding the target/motif. According to different plasmid backbone, the combination of primer 01 and 02 (SEQ ID NO: 7 and SEQ ID NO: 8) or 01 with 03 (SEQ ID NO: 7 and SEQ ID NO: 9) was selected to run PCR to insert as the targeted gene into the PD1-P24-Fc, PD1-OVA-Fc and CTLA4-P24-Fc plasmids. The PCR reactions were conducted according to standard conditions and specifically as follows: initial denaturation at 94° C. for 2 min, followed by 35 cycles of 94° C. for 15 seconds (s), 55° C. for 30 seconds, and 68° C. for 4 minutes, followed by a final extension at 68° C. for 10 minutes according to the protocol of PrimeSTAR of TAKARA (Cat. # RO10A).

Plasmids expressing PD1, HIV-1 p24, or Fc alone served as control plasmids. Plasmids were generated by restriction enzyme digestion and re-ligation, and were verified by sequencing. DNA transfected into (HEK-)293T cells was performed using polyethylenimine (PEI), and protein expression was detected by FACS using anti-rabbit Fc antibodies. Glyco-DNA motif plasmids were constructed and verified along these methods in a similar fashion. The glyco-motif sequence is depicted in FIG. 7D.

6.1.2 Mouse Immunization

All animal experiments were approved by the Committee on the Use of Live Animals in Teaching and Research at the Laboratory Animal Unit of The University of Hong Kong. Six- to eight-week-old female BALB/c mice were bred under standard pathogen-free conditions in the Laboratory Animal Unit of The University of Hong Kong. Mice were housed in cages under standard conditions with regulated temperature and humidity, fed with pelted food and tap water ad libitum, and cared for according to the criteria outlined in the Guide for the Care and Use of Laboratory Animals. The immunization procedure was similar to our previous protocols (Zhou, Cheung et al. 2013). Briefly, mice received five DNA immunizations by i.m. injection with Electroporation given every 3 weeks at a dose of 100 μg per mouse. Two weeks after every immunization, blood samples were taken for sera testing. Two weeks after the final immunization, the mice were sacrificed, and sera and splenocytes were collected for immune response analysis.

6.1.3 ELISA

Specific antibody responses were assessed by ELISA as previously described (Qi, Zhang et al. 2009). Briefly, high-affinity, protein-binding ELISA plates (Corning) were coated with HIV-1 p24 protein (Abcam). Serial diluted sera were then added and antibodies detected with HRP-labeled anti-mouse IgG BALB'c/3 mice sera) antibody (Sigma- Aldrich). Relative antibody titers were expressed as the reciprocal highest dilution of samples producing at least 2-folds greater optical density readout than that of the control serum sample at the same dilution.

6.1.4 Neutralization

All plasma samples were heat-inactivated at 56° C. for 1 hour before testing. In brief, 200 TCID50 of pseudotyped viruses was incubated with serially diluted anti-sera, in a 96-well plate in triplicate for 1 hour at 37° C. Approximately 1×10⁴ GHOST.CD4/X4/R5 cells stably transfected to express HIV-1 receptor CD4 and co-receptor CCR5 or CXCR4 as described previously were then added (Shang, Han et al. 2011), and the cultures were maintained for an additional 48 hours at 37° C. Neutralizing activity was measured by the reduction in luciferase activity compared with controls. The ID50 titers were calculated based on the standard algorithm published previously. (Brown, Frost et al. 2003).

6.1.5 Evaluation of HIV-1 Gag p24-Specific T Cell Responses

IFN-γ-producing T cells were evaluated by an ELISPOT assay (Millipore) as previously described (Zhou, Cheung et al. 2013). Ten micrograms per milliliter of HIV-1 p24 peptide (at a final concentration of 2 µg/ml for each peptide, donated by the NIH, Catalog No. 8117) were used to stimulate splenocytes in vitro. Peptide GAG A-I (AMQM-LKDTI) (SEQ ID NO: 10) is specific to CD8+ T cells, whereas peptide GAG 26 (TSNPPIPVGDIYKRWIILGL) (SEQ ID NO: 11) is specific to CD4+ T cells. Cells stimulated with 500 ng/ml phorbol 12-mystrate 13-acetate (PMA; Sigma-Aldrich) plus 1 µg/ml calcium ionocymin or left in media only served as positive and negative controls, respectively. Cells were incubated at 37° C., 5% CO2, and 100% humidity for 20 hours. Spots were identified by an immunospot reader and image analyzer (Thermo Scientific). Tetramer-positive CD8+ T cell populations were evaluated using PE-conjugated MHC class I tetramer H2d-Kd-AMQMLKDTI (SEQ ID NO: 12) (Beckman Coulter).

6.1.6 Endo H Digestion

Five micrograms of purified gp120 was denatured by heating reaction at 100° C. for 10 minutes and then was treated with 500 units of Endo H at 37° C. for 1 hour following the recommended procedures of the vendor (New England Biolabs, Ipswich, Mass.). The samples were then subjected to SDS-PAGE and Western blot analysis.

6.1.7 Western Blotting

The above 5 µg protein was separated by electrophoresis in a 7.5% polyacrylamide gel and transferred to PVDF membrane, which was incubated overnight with a 200 dilution of serum or plasma. The antigen-antibody reaction was detected by either horseradish peroxidase (HRP)-tagged anti-human or anti-mice globulin (Santa Cruz biotechnology) and 3,3'-diaminobenzidine tetrahydrochloride dehydratesubstrate.

6.2.1 Proof of Concept: DNA Motif Immunization

1) Sequencing the DNA Motif Plasmid

After construction of DNA motif plasmid library of PPMC, POMC and CPMC (FIG. 1A), the sequencing results showed that amino acid residues GPG were located at the center of inserted gene and that the flanking sequence was constituted by random amino acid residues (FIG. 1B). It indicates that DNA motif plasmid library was constructed with containing GPG motif.

2) Characterizing the Plasmid Expression

The result showed that the library plasmid of PPMC, POMC and CPMC all expressed the similar level of protein in the transfected 293T cells; the positive cells all could reach about 30% with similar level to the positive control PPC (FIG. 2). It shows that such plasmids can express protein in eukaryotic cell.

3) Characterizing Anti-Sera Titer

The fifth DNA motif plasmid generated high titer anti-sera against p24. The group of PPMC and CPMC all induced more than 20,000 dilution of anti-sera against P24. Meanwhile, POMC also induce high titer anti-sera binding with P24 in spite of the fact that the plasmid does not contain the gene of P24 (FIG. 3A). It was previously indicated that V3M01 could induce anti-sera by binding with P24 containing GPG epitope in the C-terminal, and the present plasmids and methods considered that the epitope of GPG P24 in the C-terminal contributed to anti-sera of POMC bound with P24 (Zhiwei 2012). In addition, all three anti-sera generated by plasmids PPMC, CPMC and POMC can bind with gp160 of JR-FL and ADA expressed on the cell surface, while all failed to bind the protein of Mulv as negative control (FIG. 3B). These results indicate that high titer anti-sera against P24 and gp160 were induced by PPMC group specific for epitope of GPG.

4) Characterization of Anti-Sera Neutralization

The anti-sera generated by using PPMC, POMC and CPMC plasmids as immunogens all exhibited broad neutralization against different subtypes of HIV (FIG. 4B). In contrast to anti-sera from the group of POMC and CPMC, the anti-sera of PPMC neutralized various subtypes of HIV pseudovirus containing GPG in the V3 tip like subtype B, B', B'C CRF01AE, AE CRF08BC; though it failed to neutralize CNE11 with GLG in the V3 tip and showed no neutralization against the negative control virus, VSV-G (FIGS. 4A and 4B). These data further suggest that the PPMC plasmid performed neutralization specific for GPG epitope. The results also show that the anti-sera of PPMC can neutralize not only a chronic virus but also a transmitted/founder virus like Ch40. The R5 and X4 HIV virus both can be neutralized by PPMC plasmid generated anti-sera. In addition, the dilution of ND50 of PPMC was more than 40 dilutions, which indicates that using the PPMC as an immunogen can provide protection against viral infection when used as a vaccine (Mascola and Montefiori 2010). Above all, it indicates that PPMC can induce bNAbs against various types of HIV containing GPG amino acid residues in the tip of V3 loop.

5) Characterization of Cellular Immunity

FACS results showed that PBMC from PPMC group contained 2.57-5.76% CD8⁺T specific for the epitope of AMQMLKDTI (SEQ ID NO: 12). 0.67-1.63% specific CD8+T cell was identified in the PBMC of group CPMC. As expected, the specific CD8⁺T cell was less than 1% in the PBMC from the group of POMC and negative control, as the POMC group motif antigen contained the epitope of ovalbumin instead of P24, and thus it was reasonable that the specific CD8+T cell for P24 peptide epitope was less than 1% as the PBS group (FIG. 5). Elispot experiment showed that the group of PPMC and CPMC can elicit IFN-γ+ against specific CD8 and CD4 epitope of P24 compared with the group of POMC and PBS (FIGS. 6A-B). In all, it suggests that PPMC and CPMC can induce robust cellular immunity against P24 of HIV.

Out of the presently tested plasmids, the PPMC is indicated to be a preferred candidate DNA motif vaccine against HIV infection since it is capable of inducing bNAbs and robust cellular immunity. In addition, this was the first time to prove the concept of DNA motif immunization. It indicates DNA motif immunization is effective to induce humoral and cellular immunity.

6.2.2 Glyco-DNA Motif Introduction

1) Sequencing the DNA Motif Plasmid

In accordance with one or more embodiments, there are several bNAbs such as 2G12, PG9 and PGT128 which bound with polysaccharide on HIV particle. For example, PG9 interacted with the polysaccharide of N160, 2G12 recognized the polysaccharide of N295, and the polysaccharide of N332 was involved binding with PGT128. Such different polysaccharide domains were aligned among 4633 different isolated HIV sequences from the HIV database (FIG. 7A-C). According to the alignment results, it shows that the amino acid residues related with glycosylation motif sites were highly conserved. These conserved sequences were chosen to construct glyco-DNA motif plasmid libraries as described for the PPMC plasmid construction. Six groups of glyco-DNA motif plasmid libraries were constructed as shown in FIG. 7D.

Primers used for the construction of Glyco-DNA motif plasmids can include 160M01-F, 160M02-F, 160M03-F, 295M01-F, 332M01-F, and 332M02-F, which are shown below:

```
Glyco-DNA motif plasmid PCR primers (5'-3'):
160M01-F
                                          (SEQ ID NO: 13)
AACTGCTCCTTCAACATCACCACCNNBNNBNNBNNBNNBNNBATCCTGAT

GCAGTACATCAAGG

160M02-F
                                          (SEQ ID NO: 14)
AACNNBTCCNNBAACNNBACCACCNNBNNBNNBNNBNNBNNBATCCTGAT

GCAGTACATCAAGG

160M03-F
                                          (SEQ ID NO: 15)
NNBNNBTCCNNBAACNNBACCACCNNBNNBNNBNNBNNBNNBATCCTGAT

GCAGTACATCAAGG

295M01-F
                                          (SEQ ID NO: 16)
ATCAACTGCACCCGCCCCNNBNNBNNBNNBNNBNNBATCCTGATGCAGTA

CATCAAGG

332M01-F
                                          (SEQ ID NO: 17)
GCCCACTGCAACATCTCCNNBNNBNNBNNBNNBNNBATCCTGATGCAGTA

CATCAAGG

332M02-F
                                          (SEQ ID NO: 18)
GCCNNBTGCAACNNBTCCNNBNNBNNBNNBNNBNNBATCCTGATGCAGTA

CATCAAGG

The primer
backward
                                          (SEQ ID NO: 19)
VNN VNN VNN VNN VNN VNN CTCGAGCGGAGGGGAAACA
```

The native configuration of polysaccharide epitope can be presented to the immune system via such glyco-DNA motif immunization. After construction of the glyco-DNA motif plasmid libraries, the plasmid libraries were sequenced and the inserted motif genes encoding the protein motif sequences were aligned (FIGS. 8A-F). The sequencing alignment results were as expected, in which the inserted motif gene was fixed and conserved in the center of sequence, and there were random amino acid residues encoded by the nucleic acids flanking the targeted gene. This indicates that the glyco-DNA motif plasmid libraries were successfully established with targeted glycosylation motif sites at the center of the sequence.

2) Characterizing the Plasmid Expression

FACS result showed that the glyco-DNA motif library plasmids all present similar percent positive cells expressing protein as the positive control which was transfected by the plasmid of PPC in the transfected 293T cells; with the percent positive cells all reaching about 30% (FIG. 9). It suggests that such glyco-DNA motif plasmids can also express protein in eukaryotic cells and the inserted glyco-DNA motif had no effect on protein expression. These results also suggest that the inserted motif gene of glyco-DNA motif can be expressed with the addition of polysaccharide in that the downstream of Fc protein was expressed which was verified by FACS.

3) Characterizing Anti-Sera Titer and Neutralization

The fifth glyco-DNA motif plasmid library all generated high titer anti-sera against p24 (FIG. 10A). It indicates that such plasmids elicit humoral immunity when used as an immunogen. The anti-sera extracted from mice were conducted to pseudovirus neutralization against different subtypes of HIV. VRC01 was taken as a positive control and anti-sera from PBS group was taken as a negative control (FIG. 10B). The anti-sera from glyco-DNA motif plasmid 160M01 group show the best neutralization compared to anti-sera from other groups when considering the neutralization potency and breadth. The anti-sera generated from glyco-DNA motif plasmid 160M01 neutralized all four HIV Pseudovirus including two chronic viruses of CNE15 and ADA and two transmitted/founder viruses of Ch08 and Pv04. It also failed to show better neutralization against the negative Mulv virus in contrast to anti-sera from negative control. This result suggests that 160M01 glyco-DNA motif plasmid library can be an HIV-1 candidate vaccine.

4) Characterization 160M01 Anti-Sera Polysaccharide Epitope.

To test whether 160M01 anti-sera was specific for polysaccharide of HIV gp120, western-blot was conducted. The results showed that 160M01 anti-sera binds with four divert subtypes of gp120 in lane 1, 3, 5 and 7, respectively; while there were no bands in lanes 2, 4, 6 and 8, in which the polysaccharide of four divert subtypes of gp120 was removed by the enzyme Endo H (FIG. 11A). To confirm that the protein in lane 2, 4, 6 and 8 was located in the membrane, the antibody was washed with stripping buffer and then incubated with anti-sera from HIV positive patient. All lanes show bands and the band appeared the lower location in lanes 2, 4, 6 and 8 in contrast to the band location in lanes 1, 3, 5 and 7, suggesting that Endo H enzyme only removes the polysaccharide of gp120 leading to the reduction of protein weight (FIG. 11B). Taken together, Anti-sera from 160M01 group can bind with gp120 with the help of polysaccharide. Thus, 160M01 glyco-DNA motif plasmid library successfully induces antibodies specific for the native polysaccharide.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, and publications are cited throughout this application, the disclosures of which, particularly, including all disclosed chemical structures, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

Abbreviations

PPMC: PD1-P24-Motif-Cycle-plasmid
POMC: PD1-OVA-Motif-Cycle-plasmid
CPMC: CTLA4-OVA-Motif-Cycle-plasmid
PPC: PD1-P24-Cycle-plasmid
ID50: inhibition dose of 50%
DEAE: diethylaminoethyl
PEI: polyethylenimine
HIV: human immunodeficiency virus
AIDS: acquired immunodeficiency syndrome
ELISA: Enzyme-linked immunosorbent assay
Amino Acid Motif Sequences

```
(SEQ ID NO: 1)
xxxxxNCSFNITTxxxx,
(SEQ ID NO: 2)
xxxxxNxSxNxTTxxxx,
(SEQ ID NO: 3)
xxxxxxxSxNxTTxxxx,
(SEQ ID NO: 4)
xxxxxINCTRPxxxxx,
(SEQ ID NO: 5)
xxxxxAHCNISxxxxx,
(SEQ ID NO: 6)
xxxxxAxCNxSxxxxx
(SEQ ID NO: 10)
Peptide GAG A-I (AMQMLKDTI)

(SEQ ID NO: 11)
peptide GAG 26 (TSNPPIPVGDIYKRWIILGL)

(SEQ ID NO: 12)
H2d-Kd-AMQMLKDTI
```

Nucleic Acid and Primer Sequences

The primer 01 Fc Forward
(SEQ ID NO: 7)
5' (GGC CCCGGC NNB NNB NNB NNB NNB NNB

ATCCTGATGCAGTACATCAAGG) 3'

The primer 02 P24 backward
(SEQ ID NO: 8)
5' (VNN VNN VNN VNN VNN VNN

CTCGAGCGGCAAAACTCTTG) 3'

-continued

The primer 03 OVA backward
(SEQ ID NO: 9)
5' (VNN VNN VNN VNN VNN VNN

CTCGAGCGGAGGGGAAACA) 3'

Glyco-DNA motif plasmid PCR primers (5'-3'):
160M01-F
(SEQ ID NO: 13)
AACTGCTCCTTCAACATCACCACCNNBNNBNNBNNBNNBNNBATCCTGAT

GCAGTACATCAAGG

160M02-F
(SEQ ID NO: 14)
AACNNBTCCNNBAACNNBACCACCNNBNNBNNBNNBNNBNNBATCCTGAT

GCAGTACATCAAGG

160M03-F
(SEQ ID NO: 15)
NNBNNBTCCNNBAACNNBACCACCNNBNNBNNBNNBNNBNNBATCCTGAT

GCAGTACATCAAGG

295M01-F
(SEQ ID NO: 16)
ATCAACTGCACCCGCCCCNNBNNBNNBNNBNNBNNBATCCTGATGCAGTA

CATCAAGG

332M01-F
(SEQ ID NO: 17)
GCCCACTGCAACATCTCCNNBNNBNNBNNBNNBNNBATCCTGATGCAGTA

CATCAAGG

332M02-F
(SEQ ID NO: 18)
GCCNNBTGCAACNNBTCCNNBNNBNNBNNBNNBNNBATCCTGATGCAGTA

CATCAAGG

The primer backward
(SEQ ID NO: 19)
VNN VNN VNN VNN VNN VNN CTCGAGCGGAGGGGAAACA

REFERENCES

Brown, A. J. L., S. D. W. Frost, W. C. Mathews, K. Dawson, N. S. Hellmann, E. S. Daar, D. D. Richman and S. J. Little (2003). "Transmission fitness of drug-resistant human immunodeficiency virus and the prevalence of resistance in the antiretroviral-treated population." Journal of Infectious Diseases 187(4): 683-686.

Lustig J V, Rieger H L, Kraft S C et al. "Humoral and cellular responses to native antigen following oral and parenteral immunization with lipid-conjugated bovine serum albumin." Cell Immunol. 1976 Jun. 1; 24(1): 164-72.

Mascola, J. R. and D. C. Montefiori (2010). "The Role of Antibodies in HIV Vaccines." Annual Review of Immunology, Vol 28. Palo Alto, Annual Reviews. 28: 413-444.

Mowat A M, Donachie A M, Reid G, Jarrett O. "Immune-stimulating complexes containing Quil A and protein antigen prime class I MHC-restricted T lymphocytes in vivo and are immunogenic by the oral route." Immunology. 1991 March; 72(3): 317-22.

Pearson W R, Lipman D J. "Improved tools for biological sequence comparison." Proc Natl Acad Sci. 1988; 85: 2444-2448.

Qi, Y., B. Q. Zhang, Z. Shen and Y. H. Chen (2009). "Candidate Vaccine Focused on a Classical Swine Fever Virus Epitope Induced Antibodies with Neutralizing Activity." Viral Immunology 22(3): 205-213.

Shang, H., X. Han, X. Shi, T. Zuo, M. Goldin, D. Chen, B. Han, W. Sun, H. Wu, X. Wang and L. Zhang (2011). "Genetic and Neutralization Sensitivity of Diverse HIV-1 env Clones from Chronically Infected Patients in China." Journal of Biological Chemistry 286(16): 14531-14541.

Thompson J D, Higgins D G, Gibson T J. "CLUSTAL W: improving the sensitivity of progressive multiple sequence alignment through sequence weighting, position-specific gap penalties and weight matrix choice." Nucleic Acids Res. 1994 Nov. 11; 22(22): 4673-80.

Ulmer J B, Donnelly J J, Parker S E, et al. (1993). "Heterologous protection against influenza by injection of DNA encoding viral protein." Science 259(5102):1745-1749.

WO2013/040564; Zhiwei, W. X., WU; (2012). Antibody recognizing arbitrarily designed epitope of three or more amino acid residues in a peptide and method of generating thereof.

Zhou, J., A. K. Cheung, Z. Tan, H. Wang, W. Yu, Y. Du, Y. Kang, X. Lu, L. Liu, K. Y. Yuen and Z. Chen (2013). "PD1-based DNA vaccine amplifies HIV-1 GAG-specific CD8+ T cells in mice." Journal of Clinical Investigation.

What is claimed is:

1. An immunogenic composition comprising:
a mixture of different plasmids, each of which encodes a motif peptide comprising the sequence xxxxxNCSF-NITTxxxx (SEQ ID NO: 1), wherein x stands for any amino acid residue, and wherein the x residues flanking NCSFNITT motif are different when compared to another plasmid in the mixture.

2. The immunogenic composition of claim 1, wherein the motif peptide is modified to add host-derived carbohydrates on an amino acid residue of Asparagine (N).

3. The immunogenic composition of claim 1, further comprising a sequence consisting of SEQ ID NO: 13.

4. The immunogenic composition of claim 1, wherein the plasmids are PD1-p24 plasmids with a pVAX backbone.

5. A method of inducing an immune response in a patient comprising administering the immunogenic composition of claim 1.

6. A kit comprising a therapeutically effective amount of the immunogenic composition of claim 1.

7. The kit of claim 6, further comprising a sequence consisting of SEQ ID NO: 13.

8. The immunogenic composition of claim 1, further comprising one or more primers selected from the group consisting of SEQ ID NO: 14, 15, 16, 17, 18, and 19.

9. The kit of claim 6, wherein the kit further comprises one or more primers selected from the group consisting of SEQ ID NO: 14, 15, 16, 17, 18, and 19.

* * * * *